US008263631B2

(12) United States Patent
Fujiwara et al.

(10) Patent No.: US 8,263,631 B2
(45) Date of Patent: Sep. 11, 2012

(54) ANTI-CANCER PHARMACEUTICAL COMPOSITIONS AND METHODS FOR TREATING PATIENTS WITH CANCER

(75) Inventors: Kosaku Fujiwara, Chofu (JP); Naomi Shimazaki, Kawasaki (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 549 days.

(21) Appl. No.: 12/221,019

(22) Filed: Jul. 30, 2008

(65) Prior Publication Data

US 2009/0028868 A1 Jan. 29, 2009

Related U.S. Application Data

(63) Continuation-in-part of application No. PCT/JP2007/052178, filed on Feb. 8, 2007.

(30) Foreign Application Priority Data

Feb. 9, 2006 (JP) ................................. 2006-031791

(51) Int. Cl.
*A61K 31/425* (2006.01)
*A61K 31/427* (2006.01)
*A01N 43/78* (2006.01)
*C07D 417/00* (2006.01)
*C07D 417/02* (2006.01)

(52) U.S. Cl. ........ 514/365; 514/366; 514/367; 514/368; 514/369

(58) Field of Classification Search .................. None
See application file for complete search history.

(56) References Cited

U.S. PATENT DOCUMENTS 6,432,993 B1  8/2002  Fujita et al.

FOREIGN PATENT DOCUMENTS

| EP | 1 022 272 A1 | 7/2000 |
|---|---|---|
| EP | 1 424 080 A1 | 6/2004 |
| JP | 2003-192592 A | 7/2003 |
| JP | 2003-238406 A * | 8/2003 |
| JP | 2004-083558 A | 3/2004 |
| JP | 2004-083574 A | 3/2004 |
| JP | 2004-315404 A | 11/2004 |
| JP | 2005-162727 A | 6/2005 |
| WO | WO 01/32155 A2 | 5/2001 |
| WO | WO 02/05791 A2 | 1/2002 |
| WO | WO 03/007988 A1 | 1/2003 |
| WO | WO 03/032988 A1 | 4/2003 |
| WO | WO 03/035047 A2 | 5/2003 |
| WO | WO 03/053440 A1 | 7/2003 |
| WO | WO 03/82272 A1 | 10/2003 |
| WO | WO 03/082865 A1 | 10/2003 |
| WO | WO 03/106417 A1 | 12/2003 |
| WO | WO 04/000356 A1 | 12/2003 |
| WO | WO 2004/083167 A | 9/2004 |
| WO | WO 2007/091622 A1 | 8/2007 |

OTHER PUBLICATIONS

Byers, T. (CA Cancer Journal, vol. 49, No. 6, Nov./Dec. 1999).*
Nemenoff and Winn (Europ. J. Cancer, 2005, 41: 2561-2568).*
Konopleva et al. (Molecular Cancer Therapeutic 2004, 3: 1249-1262).*
Mahtouk et al. (Oncogene 2005 24:3512-3524).*
AskOxford.com (prophylaxis, Compact Oxford English Dictionary, 2010).*
English language translation of Written Opinion of the International Searching Authority (4 pages) for PCT/JP2007/052178.
B.M. Spiegelman, "PPAR-γ: Adipogenic Regulator and Thiazolidinedione Receptor", *Diabetes*, vol. 47, pp. 507-514 (1998).
J.M. Lehmann et al, "An Antidiabetic Thiazolidinedione is a High Affinity Ligand for Peroxisome Proliferator-activated Receptor γ(PPARγ)", *J. Biol. Chem.*, vol. 270, No. 2, pp. 12953-12956 (1995).
E. Mueller et al, "Terminal Differentation of Human Breast Cancer Through PPARγ", *Molecular Cell*, vol. 1, pp. 465-470 (Feb. 1998).
T. Yoshizumi et al, "Thiazolidinediione, a peroxisome proliferator-activated receptor-γ ligand, inhibits growth . . . ", *Int. J. Oncol.*, vol. 25, pp. 631-639 (2004).
D.M. Ray et al, "Human multiple myeloma cells express peroxisome proliferator-activated receptor γ and undergo apoptosis . . . ", *Clin. Immunology*, vol. 113, pp. 203-213 (2004). T. Dwight et al, "Involvment of the PAX8/Peroxisome Proliferator-Activated Receptor γ Rearrangement in Follicular Thyroid Tumors", *J. Clin. Endocrinol. Metab*, vol. 88, pp. 4440-4445 (2003).
P. Sarraf et al, "Loss-of-Function Mutations in PPARγ Associated with Human Colon Cancer", *Molecular Cell*, vol. 3, pp. 799-804 (Jun. 1999).
G. Debrock et al, "A phase II trial with rosiglitazone in liposarcoma patients", *Br. J. Cancer*, vol. 89, pp. 1409-1412 (2003).
Strumerg D., "Preclinical and clinical development of the oral multikinase inhibitor sorafenib in cancer treatment", Drugs of Today 200512 ES, Dec. 2005, pp. 773-784, vol. 41, No. 12, XP002575457, ISSN. 0025-7656.
T. Saito, Development of Drug Therapy for Cancer and Evaluation of Effciency, Realize Inc., pp. 128-138 (1985).

* cited by examiner

*Primary Examiner* — Peter J Reddig
(74) *Attorney, Agent, or Firm* — Holtz, Holtz, Goodman & Chick, PC

(57) ABSTRACT

Method of treating persons having carcinoma, sarcoma or hematopoietic cancer by administering (i) a compound of the formula (I)

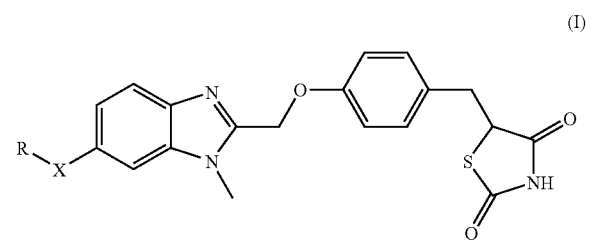

(I)

and (ii) an epidermal growth factor receptor (EGFR) inhibitor, a vascular endothelial growth factor receptor (VEGFR) inhibitor and pharmaceutical compositions for use in said method. A method for treating gastric cancer, colon cancer, lung cancer, breast cancer, pancreas cancer, kidney cancer, prostate cancer, medulloblastoma, rhabdomyosarcoma, Ewing sarcoma, liposarcoma, multiple myeloma and leukemia by administering a compound of the formula (I).

2 Claims, 5 Drawing Sheets

ANTI-CANCER PHARMACEUTICAL COMPOSITIONS AND METHODS FOR TREATING PATIENTS WITH CANCER

This application is a continuation-in-part application of international application PCT/JP2007/052178 filed Feb. 8, 2007, which is hereby incorporated by reference.

TECHNICAL FIELD

The present invention relates to (a) an anti-cancer pharmaceutical composition which contains a thiazolidinedione compound having a peroxisome proliferators activated receptor (PPAR)γ activation potency as an active ingredient, and to (b) an anti-cancer pharmaceutical composition for prophylaxis or treatment of carcinoma, sarcoma or hematopoietic cancer which contains (i) a compound having a PPARγ activation potency and (ii) an epidermal growth factor receptor (EGFR) inhibitor, a vascular endothelial growth factor receptor (VEGFR) inhibitor or a Raf kinase inhibitor as active ingredients.

The present invention also relates to a method of treating a person having specified cancers by administering to said person a thiazolidinedione compound having a peroxisome proliferators activated receptor (PPAR)γ activation potency. The present invention further relates to a method for the prophylaxis or treatment of a person having a carcinoma, sarcoma or hematopoietic cancer by administering to said person (i) a compound having a PPARγ activation potency and (ii) at least one drug selected from epidermal growth factor receptor (EGFR) inhibitor, a vascular endothelial growth factor receptor (VEGFR) inhibitor or a Raf kinase inhibitor.

BACKGROUND ART

It is widely known that PPARγ activators are useful as therapeutic drugs for type 2 diabetes mellitus, as seen in examples such as rosiglitazone and pioglitazone. PPARγ is considered to have various physiological functions such as inducement of differentiation into adipocytes and adjustment of biogenic energy metabolism (for example, refer to Non-patent Documents 1 and 2). On the other hand, it has been reported that PPARγ activators induce differentiation, cell cycle inhibition or apotosis against certain types of cancer cells, and cause growth inhibition of cancer cells (for example, refer to Non-patent Documents 3, 4 and 5). In addition to these findings, since chromosomal translocation of PAX8-PPARγ has been frequently observed and the function of PPARγ is inactivated in thyroid cancer, and since a point mutation which causes dysfunction, though not high in frequency, is observed in colon cancer, it has been suggested that PPARγ acts in an inhibitory manner against oncogenic transformation (for example, refer to Patent Documents 6 and 7). From these findings, the possibility of PPARγ activator potency for treating cancer has been considered, and small clinical tests have been conducted with cancer patients by using rosiglitazone. However, sufficient efficiency was not observed (for example, refer to Patent Document 8). Thus far, the reason for this result has not been discovered; however, it is highly likely that the anti-cancer effect by rosiglitazone was not strong enough. Accordingly, finding a PPARγ activator which has a stronger anti-cancer effect is expected to contribute greatly to the treatment of cancer in future.

On the other hand, in recent cancer treatments, an approach in which a plurality of anti-cancer drugs are used in combination to increase the efficiency of the drugs and to reduce side effects, compared with the case where each of the drugs is administered separately, has been attempted. As types of anti-cancer drugs used in combination treatment, cytocidal cancer chemotherapy drugs and various molecular target drugs that have been newly introduced to the market recently, can be mentioned. In particular, molecular target drugs are generally low in side effects compared with the former, and it is often the case that there is no need to decrease the usage amount of the former to prevent side effects from increasing, with respect to combination administration. Therefore, in combination therapy, since the efficiency of cytocidal cancer chemotherapy drugs can be obtained to the maximum and since their effect can be enhanced by the drug efficacy of molecular target drugs, development of various drugs that target molecules is conducted extensively at present. Examples of molecular target drugs which are presently gaining attention are bevacizumab (product name Avastin) which is an antibody medicament having anti-angiogenesis activity, and gefitinib (product name Iressa) and erlotinib (product name Tarceva), which are epidermal growth factor receptor (EGFR) inhibitors. In addition, sorafenib, which has anti-angiogenesis (vascular endothelial growth factor receptor (VEGFR) inhibitory) activity in combination with Raf kinase inhibitory activity and is presently in the stage of clinical testing, is also suggested to have efficiency in clinical tests and is gaining attention. As described, the indication that anti-cancer effects can be enhanced by combination administration with these molecular target drugs enables various treatment options to be provided to a patient when considering a cancer treatment, and thus greatly contributes to improvement in treatment outcome. Here, the enhancement of anti-cancer efficiency by combination administration generally indicates that the efficiency obtained by combination administration is superior to the efficiency obtained by single administration of each drug (for example, refer to Non-patent Document 9), and the clinical significance is considered to be large even when a synergistic enhancing effect cannot be obtained.

Japanese Patent No. 3488099 (for others, refer to Patent Documents 1 and 2) discloses a thiazolidinedione compound having a novel chemical structure. A compound represented by the general formula (I), which is contained as an active ingredient of the anti-cancer pharmaceutical composition according to the present invention, is a compound which is embraced in the scope of compounds relating to the thiazolidinedione compound disclosed in the patent. Japanese Patent No. 3488099 discloses that the thiazolidinedione compound disclosed in the published patent has PPARγ activation potency and can be used as an anti-cancer drug. However, the patent does not disclose any specific test data which shows that the thiazolidinedione compound actually has an anti-cancer action.

Further, pharmaceutical compositions which contain this thiazolidinedione compound and another drug have been reported.

For example, a pharmaceutical composition containing this thiazolidinedione compound and a MAP kinase inhibitor has been reported (refer to Patent Documents 3 and 4), and it is disclosed that this pharmaceutical composition is useful as a preventive drug, a therapeutic drug or as a cell proliferation inhibitor of cancer such as gastric cancer, lung cancer, breast cancer, colon cancer, prostate cancer, pancreatic cancer, liver cancer, leukemia, head and neck cancer or liposarcoma.

In addition, a pharmaceutical composition for prophylaxis or treatment of cancer which contains some of the compounds included in the scope of compounds relating to the aforementioned thiazolidinedione compound and a RXR (retinoid X receptor) activator has been reported (refer to Patent Documents 5 and 6), and it is disclosed that this pharmaceutical composition is useful as a therapeutic drug or as a preventive drug for especially lung cancer, gastric cancer or colon cancer.

A pharmaceutical composition containing the aforementioned thiazolidinedione compound and a fluorouracil type antimetabolite or a platinum complex has been reported (refer to Patent Documents 7 and 8), and it is disclosed that this pharmaceutical composition is useful especially as a preventive drug, a therapeutic drug or as a cell proliferation inhibitor of cancer such as gastric cancer, lung cancer, breast cancer, colon cancer, prostate cancer, pancreatic cancer, liver cancer, leukemia, head and neck cancer or liposarcoma.

A pharmaceutical composition containing the aforementioned thiazolidinedione compound and a diuretic drug has been reported (refer to Patent Documents 9 and 10), and it is disclosed that this pharmaceutical composition can prevent or treat side effects that are caused when PPARγ activator is administered, such as hypercardia, edema, fluid retention, and pleural effusion retention, and is useful especially as a preventive drug, a therapeutic drug or as a cell proliferation inhibitor of cancer such as gastric cancer, lung cancer, breast cancer, colon cancer, prostate cancer, pancreatic cancer, liver cancer, leukemia, head and neck cancer or liposarcoma.

A pharmaceutical composition containing the aforementioned thiazolidinedione compound and a novel sulfamide compound having MEK inhibitory activity has been reported (refer to Patent Documents 11 and 12), and it is disclosed that this pharmaceutical composition is useful especially as a preventive drug, a therapeutic drug or as a cell proliferation inhibitor of cancer such as gastric cancer, lung cancer, breast cancer, colon cancer, prostate cancer, pancreatic cancer, liver cancer, leukemia, head and neck cancer or liposarcoma.

[Patent Document 1] U.S. Pat. No. 6,432,993
[Patent Document 2] EP Patent No. 1022272
[Patent Document 3] Japanese Patent Application (Kokai) No. 2003-192592
[Patent Document 4] Pamphlet of International Publication No. WO 03/032988
[Patent Document 5] Japanese Patent Application (Kokai) No. 2003-238406
[Patent Document 6] Pamphlet of International Publication No. WO 03/053440
[Patent Document 7] Japanese Patent Application (Kokai) No. 2004-83558
[Patent Document 8] Pamphlet of International Publication No. WO 03/082865
[Patent Document 9] Japanese Patent Application (Kokai) No. 2004-83574
[Patent Document 10] Pamphlet of International Publication No. WO 2004/000356
[Patent Document 11] Japanese Patent Application (Kokai) No. 2005-162727
[Patent Document 12] Pamphlet of International Publication No. WO 2004/083167
[Non-patent Document 1] Spiegelman B M. PPAR-γ: Adipogenic regulator and thiazolidinedione receptor. Diabetes, 1998; 47: 507-14.
[Non-patent Document 2] Lehmann J M, Moore L B et al. An antidiabetic thiazolidinedione is a high affinity ligand for peroxisome proliferator-activated receptor gamma. J Biol Chem 1995; 270: 12953-6.
[Non-patent Document 3] Mueller E, Sarraf P et al. Terminal differentiation of the human breast cancer through PPAR gamma. Mol Cell 1998; 1: 465-70.
[Non-patent Document 4] Yoshizume T, Ohta T et al. Thiazolidinedione, a peroxisome proliferator-activated receptor gamma ligand, inhibits growth and metastasis of HT-29 human colon cancer cells through differentiation-promoting effects. Int J Oncol 2004; 25: 631-9.
[Non-patent Document 5] Ray D M, Bernstein S H et al. Human multiple myeloma cells express peroxisome proliferator-activated receptor γ and undergo apoptosis upon exposure to PPARγ ligands. Clin Immunology, 2004; 113: 203-13.
[Non-patent Document 6] Dwight T, Thoppe S R, et al. Involvement of the PAX8/peroxisome proliferator-activated receptor gamma rearrangement in follicular thyroid tumors. J Clin Endocrinol Metab 2003; 88: 4440-5.
[Non-patent Document 7] Sarraf P, Mueller E et al. Loss-of-function mutations in PPAR gamma associated with human colon cancer. Mol Cell 1999; 3: 799-804.
[Non-patent Document 8] Debrock G, Vanhentenrijk V et al. A phase II trial with rosiglitazone in liposarcoma patients. Br J Cancer 2003; 89: 1409-12.
[Non-patent Document 9] Tatsuo Saito ed., Development of Drug Therapy for Cancer and Evaluation of Efficiency, Realize inc., pp. 128-138 (1985).

DISCLOSURE OF THE INVENTION

Problems to be Solved by the Invention

Accordingly, the inventors of the present invention have selected a compound represented by the general formula (I), which is an active ingredient of the anti-cancer pharmaceutical composition of the present invention, from the compounds that are within the scope of the aforementioned thiazolidinedione compound, and studied the anti-cancer effects of the compound represented by the general formula (I) according to the present invention, when the compound was used alone.

As a result, it has been found that the compound represented by the general formula (I) or a pharmacologically acceptable salt thereof according to the present invention has superior anti-cancer effect against a particular type of cancer.

As a result of conducting extensive studies to find a combination of drugs having further superior anti-cancer action, the inventors of the present invention found that by administering a compound having PPARδ activation potency (especially a compound represented by the general formula (I) of the present invention) or a pharmacologically acceptable salt thereof, in combination with an epidermal growth factor receptor (EGFR) inhibitor, a vascular endothelial growth factor receptor (VEGFR) inhibitor, or a Raf kinase inhibitor, anti-cancer effects can be enhanced more than the case where they were each administered separately, and thereby completed the present invention.

Means for Solving the Problems

That is, the present invention is, (1) an anti-cancer pharmaceutical composition for prophylaxis or treatment of gastric cancer, colon cancer, lung cancer, breast cancer, pancreatic cancer, kidney cancer, prostate cancer, medulloblastoma, rhabdomyosarcoma, Ewing's sarcoma, liposarcoma, multiple myeloma or leukemia, comprising a compound represented by the following general formula (I):

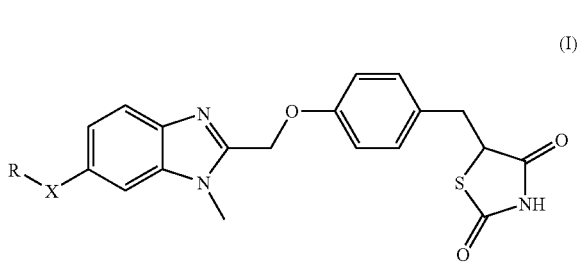

wherein,

R represents a phenyl group substituted with 1 to 5 groups selected from Substituent group α, and X represents an oxygen atom or a sulfur atom.

<Substituent group α>: a halogen atom, a hydroxy group, a $C_1$-$C_6$ alkyl group, a halogeno $C_1$-$C_6$ alkyl group, a $C_1$-$C_6$ alkoxy group, a $C_1$-$C_6$ alkylthio group, an amino group which may be substituted with 1 or 2 groups selected from Substituent group γ, a $C_3$-$C_{10}$ cycloalkyl, $C_6$-$C_{10}$ aryl, $C_7$-$C_{16}$ aralkyl, $C_6$-$C_{10}$ aryloxy, $C_7$-$C_{16}$ aralkyloxy or $C_6$-$C_{10}$ arylthio group which may be substituted with 1 to 3 groups selected from Substituent group β, a $C_1$-$C_7$ aliphatic acyloxy group, a 4- to 7-membered saturated heterocyclic group containing nitrogen atom(s), a 5- or 6-membered aromatic heterocyclic group containing nitrogen atom(s), a nitro group, and a cyano group;

<Substituent group β>: a halogen atom, a hydroxy group, a $C_1$-$C_6$ alkyl group, a halogeno $C_1$-$C_6$ alkyl group, a $C_1$-$C_6$ alkoxy group, an amino group which may be substituted with 1 or 2 groups selected from Substituent group γ, a $C_6$-$C_{10}$ aryl group, and a nitro group;

<Substituent group γ>: a $C_1$-$C_{10}$ alkyl group, a $C_6$-$C_{10}$ aryl group, a $C_7$-$C_{16}$ aralkyl group, a $C_1$-$C_7$ aliphatic acyl group, a $C_7$-$C_{11}$ aromatic acyl group, a $C_8$-$C_{12}$ aromatic-aliphatic acyl group, a $C_4$-$C_{11}$ cycloalkylcarbonyl group, and a 5- or 6-membered aromatic heterocyclic carbonyl group containing nitrogen atom(s)], or a pharmacologically acceptable salt thereof, as an active ingredient, (2) the pharmaceutical composition according to the aforementioned (1), wherein R represents a phenyl group substituted with 1 to 5 groups selected from Substituent group α, and Substituent group α is the group consisting of a halogen atom, a $C_1$-$C_6$ alkyl group, a halogeno $C_1$-$C_6$ alkyl group, an amino group which may be substituted with 1 or 2 groups selected from Substituent group γ, a 4- to 7-membered saturated heterocyclic group containing nitrogen atom(s), and a 5- or 6-membered aromatic heterocyclic group containing nitrogen atom(s), (3) the pharmaceutical composition according to the aforementioned (1), wherein R is a phenyl group substituted with one amino group which may be substituted with 1 or 2 substituents (the substituents may be the same or different, and each is a group selected from the group consisting of a $C_1$-$C_{10}$ alkyl group, a $C_6$-$C_{10}$ aryl group and a $C_7$-$C_{16}$ aralkyl group), and may be further substituted with 1 to 3 substituents (each substituent is a group selected from the group consisting of a halogen atom, a $C_1$-$C_6$ alkyl group, and a halogeno $C_1$-$C_6$ alkyl group), (4) the pharmaceutical composition according to the aforementioned (1), wherein R is a phenyl group substituted with an amino or mono- or di-$C_1$-$C_{10}$ alkylamino group, and may be further substituted with 1 or 2 $C_1$-$C_6$ alkyl groups, (5) the pharmaceutical composition according to any one of the aforementioned (1) to (4), wherein X is an oxygen atom, (6) the pharmaceutical composition according to the aforementioned (1), wherein the compound represented by the general formula (I) is a compound selected from the following:

5-(4-(6-(3-isopropylamino-phenoxy)-1-methyl-1H-benzimidazol-2-ylmethoxy)-benzyl)-thiazolidine-2,4-dione, 5-(4-(6-(3-(isobutyl-methyl-amino)-phenoxy)-1-methyl-1H-benzimidazol-2-ylmethoxy)-benzyl)-thiazolidine-2,4-dione, 5-(4-(6-(4-(isobutyl-methyl-amino)-phenoxy)-1-methyl-1H-benzimidazol-2-ylmethoxy)-benzyl)-thiazolidine-2,4-dione, 5-(4-(6-(3-(ethyl-isopropyl-amino)-phenoxy)-1-methyl-1H-benzimidazol-2-ylmethoxy)-benzyl)-thiazolidine-2,4-dione, 5-(4-(6-(4-isopropylamino-phenoxy)-1-methyl-1H-benzimidazol-2-ylmethoxy)-benzyl)-thiazolidine-2,4-dione, 5-(4-(6-(4-sec-butylamino-phenoxy)-1-methyl-1H-benzimidazol-2-ylmethoxy)-benzyl)-thiazolidine-2,4-dione, 5-(4-(6-(4-isobutylamino-phenoxy)-1-methyl-1H-benzimidazol-2-ylmethoxy)-benzyl)-thiazolidine-2,4-dione, and 5-(4-(6-(4-amino-3,5-dimethyl-phenoxy)-1-methyl-1H-benzimidazol-2-ylmethoxy)-benzyl)-thiazolidine-2,4-dione, (7) the pharmaceutical composition according to the aforementioned (1), wherein the compound represented by the general formula (I) or pharmacologically acceptable salt thereof is 5-(4-(6-(4-amino-3,5-dimethyl-phenoxy)-1-methyl-1H-benzimidazol-2-ylmethoxy)-benzyl)-thiazolidine-2,4-dione.dihydrochloride, (8) the pharmaceutical composition according to the aforementioned (1), wherein the compound represented by the general formula (I) or pharmacologically acceptable salt thereof is 5-(4-(6-(3-isopropylamino-phenoxy)-1-methyl-1H-benzimidazol-2-ylmethoxy)-benzyl)-thiazolidine-2,4-dione.dihydrochloride, (9) an anti-cancer pharmaceutical composition for prophylaxis or treatment of carcinoma, sarcoma or hematopoietic cancer, comprising:

at least one anti-cancer drug selected from the group consisting of an epidermal growth factor receptor (EGFR) inhibitor, a vascular endothelial growth factor receptor (VEGFR) inhibitor and a Raf kinase inhibitor; and at least one compound selected from the group consisting of chemical compounds represented by the following general formula (I):

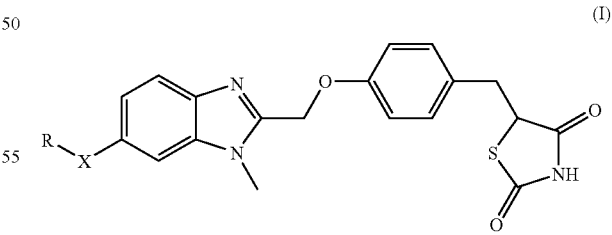

wherein

R represents a phenyl group substituted with 1 to 5 groups selected from Substituent group α; and X represents an oxygen atom or a sulfur atom;

<Substituent group α>: a halogen atom, a hydroxy group, a $C_1$-$C_6$ alkyl group, a halogeno $C_1$-$C_6$ alkyl group, a $C_1$-$C_6$ alkoxy group, a $C_1$-$C_6$ alkylthio group, an amino group which may be substituted with 1 or 2 groups selected from Substituent group γ, a $C_3$-$C_{10}$ cycloalkyl, $C_6$-$C_{10}$ aryl, $C_7$-$C_{16}$ aralkyl, $C_6$-$C_{10}$ aryloxy, $C_7$-$C_{16}$ aralkyloxy or $C_6$-$C_{10}$ arylthio group which may be substituted with 1 to 3 groups selected from Substituent group β, a $C_1$-$C_7$ aliphatic acyloxy group, a 4- to 7-membered saturated heterocyclic group containing nitrogen atom(s), a 5- or 6-membered aromatic heterocyclic group containing nitrogen atom(s), a nitro group, and a cyano group, <Substituent group β>: a halogen atom, a hydroxy group, a $C_1$-$C_6$ alkyl group, a halogeno $C_1$-$C_6$ alkyl group, a $C_1$-$C_6$ alkoxy group, an amino group which may be substituted with 1 or 2 groups selected from Substituent group γ, a $C_6$-$C_{10}$ aryl group, and a nitro group;
<Substituent group γ>: a $C_1$-$C_{10}$ alkyl group, a $C_6$-$C_{10}$ aryl group, a $C_7$-$C_{16}$ aralkyl group, a $C_1$-$C_7$ aliphatic acyl group, a $C_7$-$C_{11}$ aromatic acyl group, a $C_8$-$C_{12}$ aromatic-aliphatic acyl group, a $C_4$-$C_{11}$ cycloalkylcarbonyl group and a 5- or 6-membered aromatic heterocyclic carbonyl group containing nitrogen atom(s)], or a pharmacologically acceptable salt thereof, as active ingredients, wherein the active ingredients are for administering simultaneously or separately at different times,

(10) the pharmaceutical composition according to the aforementioned (9), wherein the anti-cancer drug is at least one selected from the group consisting of an epidermal growth factor receptor (EGFR) inhibitor (the drug being cetuximab, panitumumab, gefitinib, erlotinib or lapatinib), a vascular endothelial growth factor receptor (VEGFR) inhibitor (the drug being bevacizumab, sorafenib, SU11248 or vatalanib) and a Raf kinase inhibitor (the drug being sorafenib),

(11) the pharmaceutical composition according to the aforementioned (9), wherein the anti-cancer drug is at least one selected from the group consisting of gefitinib and sorafenib,

(12) the pharmaceutical composition according to any one of the aforementioned (9) to (11), wherein the carcinoma is gastric cancer, colon cancer, lung cancer, breast cancer, pancreatic cancer, kidney cancer or prostate cancer,

(13) the pharmaceutical composition according to any one of the aforementioned (9) to (12), wherein the sarcoma is medulloblastoma, rhabdomyosarcoma, Ewing's sarcoma or liposarcoma,

(14) the pharmaceutical composition according to any one of the aforementioned (9) to (13), wherein the hematopoietic cancer is multiple myeloma or leukemia,

(15) the pharmaceutical composition according to any one of the aforementioned (9) to (14), wherein
R represents a phenyl group substituted with 1 to 5 groups selected from Substituent group α, and
Substituent group α is the group consisting of a halogen atom, a $C_1$-$C_6$ alkyl group, a halogeno $C_1$-$C_6$ alkyl group, an amino group which may be substituted with 1 or 2 groups selected from Substituent group γ, a 4- to 7-membered saturated heterocyclic group containing nitrogen atom(s), and a 5- or 6-membered aromatic heterocyclic group containing nitrogen atom(s),

(16) the pharmaceutical composition according to any one of the aforementioned (9) to (14), wherein R is a phenyl group substituted with one amino group which may be substituted with 1 or 2 substituents (the substituents may be the same or different, and each is a group selected from the group consisting of a $C_1$-$C_{10}$ alkyl group, a $C_6$-$C_{10}$ aryl group and $C_7$-$C_{16}$ aralkyl group), and may be further substituted with 1 to 3 substituents (each substituent is a group selected from the group consisting of a halogen atom, a $C_1$-$C_6$ alkyl group and a halogeno $C_1$-$C_6$ alkyl group),

(17) the pharmaceutical composition according to any one of the aforementioned (9) to (14), wherein R is a phenyl group substituted with an amino or mono- or di-$C_1$-$C_{10}$ alkylamino group, and may be further substituted with 1 or 2 $C_1$-$C_6$ alkyl groups,

(18) the pharmaceutical composition according to any one of the aforementioned (9) to (17), wherein X is an oxygen atom,

(19) the pharmaceutical composition according to the aforementioned (9), wherein the compound represented by the general formula (I) is a compound selected from the following:
5-(4-(6-(3-isopropylamino-phenoxy)-1-methyl-1H-benzimidazol-2-ylmethoxy)-benzyl)-thiazolidine-2,4-dione,
5-(4-(6-(3-(isobutyl-methyl-amino)-phenoxy)-1-methyl-1H-benzimidazol-2-ylmethoxy)-benzyl)-thiazolidine-2,4-dione,
5-(4-(6-(4-(isobutyl-methyl-amino)-phenoxy)-1-methyl-1H-benzimidazol-2-ylmethoxy)-benzyl)-thiazolidine-2,4-dione,
5-(4-(6-(3-(ethyl-isopropyl-amino)-phenoxy)-1-methyl-1H-benzimidazol-2-ylmethoxy)-benzyl)-thiazolidine-2,4-dione,
5-(4-(6-(4-isopropylamino-phenoxy)-1-methyl-1H-benzimidazol-2-ylmethoxy)-benzyl)-thiazolidine-2,4-dione,
5-(4-(6-(4-sec-butylamino-phenoxy)-1-methyl-1H-benzimidazol-2-ylmethoxy)-benzyl)-thiazolidine-2,4-dione,
5-(4-(6-(4-isobutylamino-phenoxy)-1-methyl-1H-benzimidazol-2-ylmethoxy)-benzyl)-thiazolidine-2,4-dione, and
5-(4-(6-(4-amino-3,5-dimethyl-phenoxy)-1-methyl-1H-benzimidazol-2-ylmethoxy)-benzyl)-thiazolidine-2,4-dione,

(20) the pharmaceutical composition according to the aforementioned (9), wherein at least one compound selected from the group consisting of the compounds represented by the general formula (I) or pharmacologically acceptable salt thereof is 5-(4-(6-(4-amino-3,5-dimethyl-phenoxy)-1-methyl-1H-benzimidazol-2-ylmethoxy)-benzyl)-thiazolidine-2,4-dione.dihydrochloride, and

(21) the pharmaceutical composition according to the aforementioned (9), wherein the compound selected from the group consisting of the compound represented by the general formula (I) or pharmacologically acceptable salt thereof is 5-(4-(6-(3-isopropylamino-phenoxy)-1-methyl-1H-benzimidazol-2-ylmethoxy)-benzyl)-thiazolidine-2,4-dione.dihydrochloride.

In addition, the present invention provides a method for prophylaxis or treatment of gastric cancer, colon cancer, lung cancer, breast cancer, pancreatic cancer, kidney cancer, prostate cancer, medulloblastoma, rhabdomyosarcoma, Ewing's sarcoma, liposarcoma, multiple myeloma or leukemia, which comprises administration of the pharmaceutical composition described in any one selected from the aforementioned (1) through (8) to a warm-blooded animal (preferably a human).

Further, the present invention provides a method for prophylaxis or treatment of carcinoma (especially, gastric cancer, colon cancer, lung cancer, breast cancer, pancreatic cancer, kidney cancer or prostate cancer), sarcoma (especially, medulloblastoma, rhabdomyosarcoma, Ewing's sarcoma or liposarcoma) or hematopoietic cancer (especially, multiple myeloma or leukemia), which comprises administering the active ingredients of the pharmaceutical composition simultaneously or administering each of the active ingredients at different times, the active ingredients being as described in one selected from the aforementioned (9) through (21).

In the present invention, "halogen atom" in the definition of Substituent groups α and β is a fluorine atom, chlorine atom, bromine atom or iodine atom, preferably a fluorine atom or chlorine atom, and more preferably a fluorine atom.

"$C_1$-$C_6$ alkyl group" in the definition of Substituent groups α and β represents a linear or branched alkyl group having 1 to 6 carbon atoms, and is for example, a methyl, ethyl, propyl, isopropyl, butyl, isobutyl, s-butyl, t-butyl, pentyl, isopentyl, 2-methylbutyl, neopentyl, 1-ethylpropyl, hexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl or 2-ethylbutyl group. With respect to Substituent group α, it is preferably a methyl or t-butyl group, and with respect to Substituent group β, it is preferably a $C_1$-$C_4$ alkyl group, and more preferably a methyl or ethyl group.

"Halogeno $C_1$-$C_6$ alkyl group" in the definition of Substituent groups α and β represents a group in which 1 to 3 of the aforementioned halogen atoms are bonded to the aforementioned $C_1$-$C_6$ alkyl group, and is for example, a trifluoromethyl, trichloromethyl, tribromomethyl, difluoromethyl, dichloromethyl, dibromomethyl, fluoromethyl, 2,2,2-trichloroethyl, 2,2,2-trifluoroethyl, 2-bromoethyl, 2-chloroethyl, 2-fluoroethyl, 2-iodoethyl, 3-chloropropyl, 4-fluorobutyl, 6-iodohexyl or 2,2-dibromoethyl group, preferably a halogeno $C_1$-$C_2$ alkyl group, and more preferably a trifluoromethyl group.

"$C_1$-$C_6$ alkoxy group" in the definition of Substituent groups α and β represents a group in which the aforementioned $C_1$-$C_6$ alkyl group is bonded to an oxygen atom, and is for example, a methoxy, ethoxy, propoxy, isopropoxy, butoxy, isobutoxy, s-butoxy, t-butoxy, pentoxy, isopentoxy, 2-methylbutoxy, neopentoxy, 1-ethylpropoxy, hexyloxy, 4-methylpentoxy, 3-methylpentoxy, 2-methylpentoxy, 3,3-dimethylbutoxy, 2,2-dimethylbutoxy, 1,1-dimethylbutoxy, 1,2-dimethylbutoxy, 1,3-dimethylbutoxy, 2,3-dimethylbutoxy or 2-ethylbutoxy group, preferably a $C_1$-$C_4$ alkoxy group, more preferably a $C_1$-$C_2$ alkoxy group, and especially preferably a methoxy group.

"$C_1$-$C_6$ alkylthio group" in the definition of Substituent group α represents a group in which the aforementioned $C_1$-$C_6$ alkyl group is bonded to a sulfur atom, and is for example, a methylthio, ethylthio, propylthio, isopropylthio, butylthio, isobutylthio, s-butylthio, t-butylthio, pentylthio, isopentylthio, 2-methylbutylthio, neopentylthio, 1-ethylpropylthio, hexylthio, 4-methylpentylthio, 3-methylpentylthio, 2-methylpentylthio, 1-methylpentylthio, 3,3-dimethylbutylthio, 2,2-dimethylbutylthio, 1,1-dimethylbutylthio, 1,2-dimethylbutylthio, 1,3-dimethylbutylthio, 2,3-dimethylbutylthio or 2-ethylbutylthio group, preferably a $C_1$-$C_4$ alkylthio group, more preferably a $C_1$-$C_2$ alkylthio group, and especially preferably a methylthio group.

"Amino group which may be substituted with 1 or 2 groups selected from Substituent group γ" in the definition of Substituent groups α and β represents an amino group which may be substituted with one or two groups which may be the same or different, the group being selected from Substituent group γ consisting of a $C_1$-$C_{10}$ alkyl group, a $C_6$-$C_{10}$ aryl group, a $C_7$-$C_{16}$ aralkyl group, a $C_1$-$C_7$ aliphatic acyl group, a $C_7$-$C_{11}$ aromatic acyl group, a $C_8$-$C_{12}$ aromatic-aliphatic acyl group, a $C_4$-$C_{11}$ cycloalkylcarbonyl group and a 5- or 6-membered aromatic heterocyclic carbonyl group containing nitrogen atom(s).

In the above definition, "$C_1$-$C_{10}$ alkyl group" in the definition of Substituent group γ represents a linear or branched alkyl group having 1 to 10 carbon atoms, and is for example, the aforementioned $C_1$-$C_6$ alkyl, heptyl, 1-methylhexyl, 2-methylhexyl, 3-methylhexyl, 4-methylhexyl, 5-methylhexyl, 1-propylbutyl, 4,4-dimethylpentyl, octyl, 1-methylheptyl, 2-methylheptyl, 3-methylheptyl, 4-methylheptyl, 5-methylheptyl, 6-methylheptyl, 1-propylpentyl, 2-ethylhexyl, 5,5-dimethylhexyl, nonyl, 3-methyloctyl, 4-methyloctyl, 5-methyloctyl, 6-methyloctyl, 1-propylhexyl, 2-ethylheptyl, 6,6-dimethylheptyl, decyl, 1-methylnonyl, 3-methylnonyl, 8-methylnonyl, 3-ethyloctyl, 3,7-dimethyloctyl or 7,7-dimethyloctyl group, and is preferably a linear or branched alkyl group having 1 to 4 carbon atoms.

In the above definition, "$C_6$-$C_{10}$ aryl group" in the definition of Substituent group γ represents an aromatic hydrocarbon group having 6 to 10 carbon atoms, and the group may be substituted by a nitro group, the aforementioned halogen atoms, a hydroxy group, the aforementioned $C_1$-$C_6$ alkyl group, a $C_1$-$C_6$ alkylcarbonyloxy group or a $C_1$-$C_6$ alkoxy group. Such group is for example, a phenyl, naphthyl, paranitrophenyl, parachlorophenyl, parafluorophenyl, parahydroxyphenyl, paraacetoxyphenyl, paramethylphenyl, paraethylphenyl, parapropylphenyl, paramethoxyphenyl, paraethoxyphenyl or parapropoxyphenyl group, and is preferably a phenyl, paranitrophenyl or parapropoxyphenyl group.

In the above definition, "$C_7$-$C_{16}$ aralkyl group" in the definition of Substituent group γ represents a group in which the aforementioned $C_6$-$C_{10}$ aryl group is bonded to the aforementioned $C_1$-$C_6$ alkyl group, and is for example, a benzyl, naphthylmethyl, indenylmethyl, diphenylmethyl, 1-phenethyl, 2-phenethyl, 1-naphthylethyl, 2-naphthylethyl, 1-phenylpropyl, 2-phenylpropyl, 3-phenylpropyl, 1-naphthylpropyl, 2-naphthylpropyl, 3-naphthylpropyl, 1-phenylbutyl, 2-phenylbutyl, 3-phenylbutyl, 4-phenylbutyl, 1-naphthylbutyl, 2-naphthylbutyl, 3-naphthylbutyl, 4-naphthylbutyl, 5-phenylpentyl, 5-naphthylpentyl, 6-phenylhexyl or 6-naphthylhexyl group, preferably an aralkyl group in which a phenyl group is bonded to a $C_1$-$C_4$ alkyl group, and more preferably a benzyl group.

In the above definition, "$C_1$-$C_7$ aliphatic acyl group" in the definition of Substituent group γ represents a group in which a hydrogen atom, or a saturated or non-saturated $C_1$-$C_6$ linear hydrocarbon group is bonded to a carbonyl group, and is for example, a formyl, acetyl, propionyl, butyryl, isobutyryl, valeryl, isovaleryl, pivaloyl, hexanoyl, acryloyl, methacryloyl or crotonoyl group, preferably an acetyl, propionyl or pivaloyl group, and more preferably an acetyl group.

In the above definition, "$C_7$-$C_{11}$ aromatic acyl group" in the definition of Substituent group γ represents a group in which a $C_6$-$C_{10}$ aryl group is bonded to a carbonyl group, and is for example, a benzoyl, 1-indanecarbonyl, 2-indanecarbonyl or 1- or 2-naphthoyl group, and is preferably a benzoyl or naphthoyl group.

In the above definition, "$C_8$-$C_{12}$ aromatic-aliphatic acyl group" in the definition of Substituent group γ represents a group in which a phenyl group is bonded to a $C_2$-$C_6$ aliphatic acyl group, and is for example, a phenylacetyl, 3-phenylpropionyl, 4-phenylbutyryl, 5-phenylpentanoyl or 6-phenylhexanoyl group, and is preferably a phenylacetyl group.

In the above definition, "$C_4$-$C_{11}$ cycloalkylcarbonyl group" in the definition of Substituent group γ represents a group in which a $C_3$-$C_{10}$ cycloalkyl group (which represents a 3- to 10-membered saturated cyclic hydrocarbon group which may be ring-fused, and is for example, a cyclopropyl, cyclobutyl, cyclopentyl, cyclohexyl, cycloheptyl, norbornyl or adamantyl group, and preferably a $C_3$-$C_6$ cycloalkyl group) is bonded to a carbonyl group, and is for example, a cyclopropanoyl, cyclobutyryl, cyclopentanoyl, cyclohexanoyl, cycloheptylcarbonyl, norbornylcarbonyl or adamantylcarbonyl group, preferably a $C_4$-$C_7$ cycloalkylcarbonyl group, and especially preferably a cyclopentanoyl or cyclohexanoyl group.

In the above definition, "5- or 6-membered aromatic heterocyclic carbonyl group containing nitrogen atom(s)" in the definition of Substituent group γ represents a group in which a 5- or 6-membered aromatic heterocyclic ring which contains at least one nitrogen atom and may further contain a hetero atom selected from the hetero atom group consisting of a nitrogen atom, an oxygen atom and a sulfur atom (for example, a pyrrolyl, imidazolyl, pyrazolyl, triazolyl, tetrazolyl, pyridyl, pyrazinyl, pyrimidinyl, pyridazinyl, thiazolyl, oxazolyl, oxadiazolyl or thiadiazolyl group), is bonded to a carbonyl group, and is for example, a pyrrolylcarbonyl, imidazolylcarbonyl, pyrazolylcarbonyl, triazolylcarbonyl, tetrazolylcarbonyl, nicotinoyl, isonicotinoyl, pyrazinylcarbonyl, pyrimidinylcarbonyl, pyridazinylcarbonyl, thiazolylcarbonyl, oxazolylcarbonyl, oxadiazolylcarbonyl or thiadiazolylcarbonyl group, preferably a pyridylcarbonyl group, and especially preferably a nicotinoyl or isonicotinoyl group.

"Amino group which may be substituted with 1 or 2 groups selected from Substituent group γ" in the definition of Substituent groups α and β is preferably an amino group or an amino group which is substituted with 1 or 2 substituents (the substituents are the same or different groups each selected from the group consisting of a $C_1$-$C_{10}$ alkyl group, a $C_6$-$C_{10}$ aryl group and a $C_7$-$C_{16}$ aralkyl group), more preferably an amino group or a mono- or di-$C_1$-$C_{10}$ alkylamino group, and especially preferably an amino, dimethylamino or isopropylamino group.

The $C_3$-$C_{10}$ cycloalkyl moiety of "$C_3$-$C_{10}$ cycloalkyl group which may be substituted with 1 to 3 groups selected from Substituent group β" in the definition of Substituent group a has the same meaning as described above, and is preferably a $C_3$-$C_{10}$ cycloalkyl group which may be substituted with one group selected from Substituent group β, more preferably a $C_3$-$C_{10}$ cycloalkyl group which may be substituted with one group selected from the group consisting of halogen, hydroxy, $C_1$-$C_6$ alkyl and halogeno $C_1$-$C_6$ alkyl, even more preferably an adamantyl group which may be substituted with one of fluorine, chlorine, hydroxy, methyl, ethyl, t-butyl, trifluoromethyl, methoxy, amino, methylamino or dimethylamino, and especially preferably an adamantyl group.

With respect to the "$C_6$-$C_{10}$ aryl group which may be substituted with 1 to 3 groups selected from Substituent group β" in the definition of Substituent group α and with respect to "$C_6$-$C_{10}$ aryl group" in the definition of Substituent group β, the $C_6$-$C_{10}$ aryl moiety has the same meaning as described above, and is preferably a $C_6$-$C_{10}$ aryl group which may be substituted with one group selected from Substituent group β, more preferably a $C_6$-$C_{10}$ aryl group which may be substituted with one of halogen, hydroxy, $C_1$-$C_6$ alkyl, halogeno $C_1$-$C_6$ alkyl, $C_1$-$C_6$ alkoxy or amino which may be substituted with 1 or 2 groups selected from Substituent group γ, even more preferably a phenyl group which may be substituted with one of fluorine, chlorine, hydroxy, methyl, ethyl, t-butyl, trifluoromethyl, methoxy, amino, methylamino or dimethylamino, and especially preferably a phenyl or 4-hydroxyphenyl group.

The $C_7$-$C_{16}$ aralkyl moiety of the "$C_7$-$C_{16}$ aralkyl group which may be substituted with 1 to 3 groups selected from Substituent group β" in the definition of Substituent group α, has the same meaning as described above, and is preferably a $C_7$-$C_{16}$ aralkyl group which may be substituted with one group selected from Substituent group β, more preferably a benzyl group which may be substituted with one of halogen, hydroxy, $C_1$-$C_6$ alkyl, halogeno $C_1$-$C_6$ alkyl, $C_1$-$C_6$ alkoxy or amino which may be substituted with 1 or 2 groups selected from Substituent group γ, even more preferably a benzyl group which may be substituted with one of fluorine, chlorine, hydroxy, methyl, ethyl, t-butyl, trifluoromethyl, methoxy, amino, methylamino or dimethylamino, and especially preferably a benzyl group.

The $C_6$-$C_{10}$ aryloxy moiety of the "$C_6$-$C_{10}$ aryloxy group which may be substituted with 1 to 3 groups selected from Substituent group β" in the definition of Substituent group α represents a group in which the aforementioned $C_6$-$C_{10}$ aryl is bonded to an oxygen atom, and is for example, a phenoxy, 1-indenyloxy, 2-indenyloxy, 3-indenyloxy, 1-naphthyloxy or 2-naphthyloxy group, and is preferably a phenoxy group.

The $C_7$-$C_{16}$ aralkyloxy moiety of the "$C_7$-$C_{16}$ aralkyloxy group which may be substituted with 1 to 3 groups selected from Substituent group β" in the definition of Substituent group α represents a group in which the aforementioned $C_7$-$C_{16}$ aralkyl group is bonded to an oxygen atom, and is for example, benzyloxy, naphthylmethoxy, indenylmethoxy, diphenylmethoxy, 1-phenethyloxy, 2-phenethyloxy, 1-naphthylethoxy, 2-naphthylethoxy, 1-phenylpropoxy, 2-phenylpropoxy, 3-phenylpropoxy, 1-naphthylpropoxy, 2-naphthylpropoxy, 3-naphthylpropoxy, 1-phenylbutoxy, 2-phenylbutoxy, 3-phenylbutoxy, 4-phenylbutoxy, 1-naphthylbutoxy, 2-naphthylbutoxy, 3-naphthylbutoxy, 4-naphthylbutoxy, 5-phenylpentyloxy, 5-naphthylpentyloxy, 6-phenylhexyloxy or 6-naphthylhexyloxy group, and is preferably a benzyloxy group.

The $C_6$-$C_{10}$ arylthio moiety of the "$C_6$-$C_{10}$ arylthio group which may be substituted with 1 to 3 groups selected from Substituent group β" in the definition of Substituent group α represents a group in which the aforementioned $C_6$-$C_{10}$ aryl group is bonded to a sulfur atom, and is for example, a phenylthio, 1-indenylthio, 2-indenylthio, 3-indenylthio, 1-naphthylthio or 2-naphthylthio group, and is preferably a phenylthio group.

"$C_1$-$C_7$ aliphatic acyloxy group" in the definition of Substituent group α represents a group in which the aforementioned $C_1$-$C_7$ aliphatic acyl group is bonded to an oxygen atom, and is for example, a formyloxy, acetoxy, propionyloxy, butyryloxy, isobutyryloxy, valeryloxy, isovaleryloxy, pivaloyloxy, hexanoyloxy, acryloyloxy, methacryloyloxy or crotoyloxy group, and preferably an acetoxy group.

"4- to 7-membered saturated heterocyclic group containing nitrogen atom(s)" in the definition of Substituent group α represents a 4- to 7-membered saturated heterocyclic group which contains at least one nitrogen atom and may further contain hetero-atom(s) selected from the hetero atom group consisting of a nitrogen atom, oxygen atom and sulfur atom, and is for example, an azetidinyl, pyrrolidinyl, imidazolidinyl, thiazolidinyl, pyrazolidinyl, piperidinyl, morpholinyl, thiomorpholinyl, piperazinyl or homopiperazinyl group, preferably a pyrrolidinyl, piperidinyl or morpholinyl group, and more preferably a pyrrolidin-1-yl, piperidin-1-yl or morpholin-4-yl group.

"5- or 6-membered aromatic heterocyclic group containing nitrogen atom(s)" in the definition of Substituent group α has the same meaning as described above, and is preferably an imidazolyl, tetrazolyl or pyridinyl group, and more preferably a pyridin-2-yl or pyridin-3-yl group.

R is preferably a phenyl group substituted with 1 to 5 groups selected from the group consisting of a halogen atom, a $C_1$-$C_6$ alkyl group, a halogeno $C_1$-$C_6$ alkyl group, an amino group which may be substituted with 1 or 2 groups selected from Substituent group γ, a 4- to 7-membered saturated heterocyclic group containing nitrogen atom(s) and a 5- to 6-membered aromatic heterocyclic group containing nitrogen atom(s).

R is more preferably a phenyl group which is substituted with amino or amino which is substituted with 1 or 2 substituents (the substituents are the same or different, and each is a group selected from the group consisting of a $C_1$-$C_{10}$ alkyl group, a $C_6$-$C_{10}$ aryl group and a $C_7$-$C_{16}$ aralkyl group), and may be further substituted with 1 to 3 substituents (each substituent is a group selected from a group consisting of a halogen atom, a $C_1$-$C_6$ alkyl group and a halogeno $C_1$-$C_6$ alkyl group).

R is even more preferably a phenyl group which is substituted with an amino or mono- or di-$C_1$-$C_{10}$ alkylamino group, and may be further substituted with 1 or 2 $C_1$-$C_6$ alkyl groups.

The compound represented by the general formula (I), which is an active ingredient of a pharmaceutical composition of the present invention, is preferably 5-(4-(6-(3-isopropylamino-phenoxy)-1-methyl-1H-benzimidazol-2-ylmethoxy)-benzyl)-thiazolidine-2,4-dione 5-(4-(6-(3-(isobutyl-methyl-amino)-phenoxy)-1-methyl-1H-benzimidazol-2-ylmethoxy)-benzyl)-thiazolidine-2,4-dione 5-(4-(6-(4-(isobutyl-methyl-amino)-phenoxy)-1-methyl-1H-benzimidazol-2-ylmethoxy)-benzyl)-thiazolidine-2,4-dione 5-(4-(6-(3-(ethyl-isopropyl-amino)-phenoxy)-1-methyl-1H-benzimidazol-2-ylmethoxy)-benzyl)-thiazolidine-2,4-dione 5-(4-(6-(4-isopropylamino-phenoxy)-1-methyl-1H-benzimidazol-2-ylmethoxy)-benzyl)-thiazolidine-2,4-dione 5-(4-(6-(4-sec-butylamino-phenoxy)-1-methyl-1H-benzimidazol-2-ylmethoxy)-benzyl)-thiazolidine-2,4-dione 5-(4-(6-(4-isobutylamino-phenoxy)-1-methyl-1H-benzimidazol-2-ylmethoxy)-benzyl)-thiazolidine-2,4-dione or 5-(4-(6-(4-amino-3,5-dimethyl-phenoxy)-1-methyl-1H-benzimidazol-2-ylmethoxy)-benzyl)-thiazolidine-2,4-dione, or a pharmacologically acceptable salt thereof, and further preferably 5-(4-(6-(4-amino-3,5-dimethyl-phenoxy)-1-methyl-1H-benzimidazol-2-ylmethoxy)-benzyl)-thiazolidine-2,4-dione.dihydrochloride, or 5-(4-(6-(3-isopropylamino-phenoxy)-1-methyl-1H-benzimidazol-2-ylmethoxy)-benzyl)-thiazolidine-2,4-dione.dihydrochloride.

The present invention provides an anti-cancer pharmaceutical composition for prophylaxis or treatment of carcinoma, sarcoma or hematopoietic cancer, the composition including at least one anti-cancer drug selected from the group consisting of an epidermal growth factor receptor (EGFR) inhibitor, a vascular endothelial growth factor receptor (VEGFR) inhibitor and a Raf kinase inhibitor, and at least one compound selected from the group consisting of a compound having peroxisome proliferator activated receptor (PPAR) γ activation potency or pharmacologically acceptable salt thereof as active ingredients, for administering the active ingredients simultaneously or at different times.

Epidermal growth factor receptor (EGFR) is a receptor protein which exists on the cell surface corresponding to an epidermal growth factor. The receptor is a membrane-spanning protein, and has a region within the cell where it possesses tyrosine kinase activity. It has become apparent that the receptor is expressed on the surface of many cancer cells, and frequent overexpression is observed especially in lung cancer, breast cancer, colon cancer, pancreatic cancer and the like. With respect to drugs which inhibit the function of epidermal growth factor receptor (EGFR), cetuximab (trade name Erbitux) and panitumumab can be mentioned for example as antibodies which bind with the extracellular domain. In addition, with respect to inhibitors against tyrosine kinase activity, gefitinib (trade name Iressa), erlotinib (trade name Tarceva) and lapatinib can be mentioned. Preferably, erlotinib (trade name Tarceva) can be mentioned.

Vascular endothelial growth factor receptor (VEGFR) is a receptor protein which exists on the cell surface corresponding to a vascular endothelial growth factor. The receptor is a membrane-spanning protein, and has a region within the cell where it posseses tyrosine kinase activity. It has been known that the receptor is expressed mainly in vascular endothelial cells, and promotes proliferation of vascular endothelial cells by being stimulated with vascular endothelial growth factor secreted from cancer cells. As a result, angiogenesis in the periphery of cancer tissue is enhanced, and proliferation of cancer tissues is promoted. With respect to drugs which inhibit the function of vascular endothelial growth factor receptor (VEGFR), bevacizumab (trade name Avastin) which is a neutralizing antibody against vascular endothelial cell growth factor itself, and sorafenib, SU11248 and vatalanib (PTK787) which are inhibitors against tyrosine kinase activity, can be mentioned. Preferably, sorafenib can be mentioned.

Raf kinase is one type of serine-threonine kinase which is deeply involved with cell proliferation signalling, and is known to share a role in a cascade which transduces a proliferation signal from Ras protein, which is a low molecular weight G protein, into a nucleus. With respect to drugs which inhibit kinase activity of Raf, sorafenib can be mentioned for example.

The compound having PPAR γ activation potency, which is one of the active ingredients of the aforementioned anti-cancer pharmaceutical composition according to the present invention, includes any compounds which activate human PPARγ by any acceptable assay, or any compounds which are generally recognized as PPARγ activators or as PPARγ agonists. Such PPARγ activator may be two or more PPAR subtype activators. As for preferable PPARγ activators, thiazolidinedione compounds which are known to be useful for treating diabetes, and non-thiazolidinedione compounds such as those disclosed in U.S. Pat. No. 6,294,580 can be mentioned. As for preferable thiazolidinedione compounds, currently commercially available rosiglitazone and pioglitazone, and compounds disclosed in Japanese Patent No. 2976885 (U.S. Pat. No. 5,886,014), Japanese Patent No. 3488099 (U.S. Pat. No. 6,432,993, EP Patent No. 1022272) and Japanese Patent Application (Kokai) No. 2000-351779 (International Publication No. WO 00/61581) can be mentioned in addition to the compound represented by the general formula (I) according to the present invention. As for preferable non-thiazolidinedione compounds, compounds that are under development, such as Glaxo Smith Kline's compound GI262570 (farglitazar) and the like can be mentioned. Among these compounds having a PPARγ activation potency, especially preferable are the compound represented by the general formula (I) or a pharmacologically acceptable salt thereof according to the present invention.

Among the compound represented by the general formula (I) according to the present invention, the compound having a PPARγ activation potency, the epidermal growth factor receptor (EGFR) inhibitor, the vascular endothelial growth factor receptor (VEGFR) inhibitor and the Raf kinase inhibitor, which are active ingredients of the present invention, those which form salts can each be made into a salt in accordance with general methods, and such salts are also embraced in the present invention.

Among such salts, an inorganic acid salt such as hydrochloric acid salt, hydrobromic acid salt, sulfuric acid salt, nitric acid salt and phosphoric acid salt; carboxylic acid salt such as acetic acid salt, fumaric acid salt, maleic acid salt, oxalic acid salt, malonic acid salt, succinic acid salt, citric acid salt and malic acid salt; a sulfonic acid salt such as methanesulfonic acid salt, ethanesulfonic acid salt, benzenesulfonic acid salt and toluenesulfonic acid salt; and an amino acid salt such as glutamic acid salt and asparatic acid salt; can be mentioned, for example, as a salt with an acid.

As a salt with a base, an alkali metal salt such as lithium salt, sodium salt and potassium salt; an alkaline earth metal salt such as calcium salt and magnesium salt; or an organic base salt such as ammonium salt, triethylamine salt, diisopropylamine salt and cyclohexylamine salt; can be mentioned for example.

There are cases where each of the compound represented by the general formula (I), the compound having a PPARγ activation potency, the epidermal growth factor receptor (EGFR) inhibitor, the vascular endothelial growth factor receptor (VEGFR) inhibitor and the Raf kinase inhibitor, which are each an active ingredient of the pharmaceutical composition according to the present invention, has an optical isomer, and each of such and a mixture thereof are all embraced in the present invention. Such optical isomer can be obtained by either a synthesis using a starting material of each of the isomers, or by resolution of a synthesized compound using a general resolution method or separation method if desired.

There are cases where each of the compound represented by the general formula (I), the compound having a PPARγ activation potency, the epidermal growth factor receptor (EGFR) inhibitor, the vascular endothelial growth factor receptor (VEGFR) inhibitor and the Raf kinase inhibitor, which are each an active ingredient of the pharmaceutical composition according to the present invention, exists as a hydrate or as a solvate, and each of such and a mixture thereof are all embraced in the present invention.

The present invention provides a method for prophylaxis or treatment of carcinoma (especially, gastric cancer, colon cancer, lung cancer, breast cancer, pancreatic cancer, kidney cancer or prostate cancer), sarcoma (especially, medulloblastoma, rhabdomyosarcoma, Ewing's sarcoma or liposarcoma) or hematopoietic cancer (especially, multiple myeloma or leukemia), the method for prophylaxis or treatment according to the present invention being conducted by using the compound represented by the aforementioned general formula (I) or a pharmacologically acceptable salt thereof alone, or by using a combination of a compound having PPARγ activation potency (preferably the compound represented by the aforementioned general formula (I)) or a pharmacologically acceptable salt thereof with an epidermal growth factor receptor (EGFR) inhibitor, a vascular endothelial growth factor receptor (VEGFR) inhibitor or a Raf kinase inhibitor.

In the present invention, "using a combination" means to use two or more types of drugs, and a form in which each of the drugs is administered at the same time, a form in which each of them is administered alone separately after an interval, and a form in which they are mixed and are administered as a physically uniform composition can be mentioned.

In the present invention, "administer at the same time" has no particular limitation so long as it is an administration form capable of administering substantially at the same time; however, administration as a uniform composition is preferable.

In addition, "administer separately after an interval" has no particular limitation so long as it is an administration form capable of administering separately at different times. For example, an administration form in which the epidermal growth factor receptor (EGFR) inhibitor, the vascular endothelial growth factor receptor (VEGFR) inhibitor or the Raf kinase inhibitor is administered first, and after a predetermined time, the compound having PPARγ activation potency or a pharmacologically acceptable salt thereof is administered, can be mentioned.

Effects of the Invention

The anti-cancer pharmaceutical composition of the present invention which contains a compound represented by the general formula (I) as an active ingredient, is useful as an agent for prophylaxis or treatment of gastric cancer, colon cancer, lung cancer, breast cancer, pancreatic cancer, kidney cancer, prostate cancer, medulloblastoma, rhabdomyosarcoma, Ewing's sarcoma, liposarcoma, multiple myeloma or leukemia.

The anti-cancer pharmaceutical composition according to the present invention, which includes at least one anti-cancer drug selected from the group consisting of an epidermal growth factor receptor (EGFR) inhibitor, a vascular endothelial growth factor receptor (VEGFR) inhibitor and a Raf kinase inhibitor, and at least one compound selected from the group consisting of a compound having a PPARγ activation potency and a pharmacologically acceptable salt thereof as active ingredients which are for administering simultaneously or separately at different times, is useful as an anti-cancer drug (anti-cancer drug for prophylaxis or treatment of carcinoma such as gastric cancer, colon cancer, lung cancer, breast cancer, pancreatic cancer, kidney cancer and prostate cancer, sarcoma such as medulloblastoma, rhabdomyosarcoma, Ewing's sarcoma and liposarcoma, and hematopoietic cancer such as multiple myeloma and leukemia).

BEST MODE FOR CARRYING OUT THE INVENTION

The compound represented by the general formula (I), which is an active ingredient of the pharmaceutical composition of the present invention, can be manufactured easily in accordance with the method described in Japanese Patent No. 3488099.

Rosiglitazone can be manufactured easily in accordance with the method disclosed in U.S. Pat. No. 5,741,803, and pioglitazone in accordance with U.S. Pat. No. 4,687,777.

With respect to thiazolidinedione compounds having PPARδ activation potency, which are disclosed in Japanese Patent No. 2976885 (U.S. Pat. No. 5,886,014), Japanese Patent No. 3488099 (U.S. Pat. No. 6,432,993, EP Patent No. 1022272) and Japanese Patent Application (Kokai) No. 2000-351799 (International Publication No. WO 00/61581), manufacturing methods are also disclosed in each of the published applications, and the compounds can be manufactured easily in accordance with the methods disclosed in each of the published applications.

Farglitazar can be manufactured easily in accordance with the method disclosed in International Publication No. WO 00/08002.

As an epidermal growth factor receptor (EGFR) inhibitor, which is an active ingredient of the anti-cancer pharmaceutical composition of the present invention, the composition containing a compound having PPARγ activation potency such as a compound represented by the general formula (I) or a pharmacologically acceptable salt thereof and other anti-cancer agent(s) as active ingredients, gefitinib is available from AstraZeneca.

Cetuximab can be manufactured easily in accordance with the method disclosed in EP Patent No. 359282, panitumumab in accordance with International Publication No. WO 96/33735, erlotinib in accordance with International Publication No. WO 96/30347, lapatinib in accordance with International Publication No. WO 99/35146, and among the vascular endothelial growth factor receptor (VEGFR) inhibitors, bevacizumab in accordance with EP Patent No. 1325932, sorafenib in accordance with International Publication No. WO 99/35146, SU11248 in accordance with International Publication No. WO 2001/060814, and vatalanib in accordance with International Publication No. WO 98/035958.

In the case where the compound represented by the general formula (I) or a pharmacologically acceptable salt thereof, which is an active ingredient of the pharmaceutical composition according to the present invention, is used as a therapeutic agent, a quality of life improving agent or as a prophylactic agent, the compound or a pharmacologically acceptable salt thereof by itself or in a mixture with a pharmacologically acceptable carrier, e.g., an excipient, diluent and the like that are suitably pharmacologically acceptable, can be administered orally as a tablet, a capsule, granules, powders or syrup, or parenterally by injection or suppository.

These pharmaceutical preparations are prepared in accordance with a known process by using additives including excipients (for example, organic excipients such as sugar derivatives, e.g. lactose, sucrose, glucose, mannitol or sorbitol; starch derivatives, e.g. corn starch, potato starch, α-starch or dextrin; cellulose derivatives, e.g. crystalline cellulose; gum arabic; dextrane; or pullulan, and inorganic excipients such as silicate derivatives, e.g. light silicic anhydride, synthetic aluminum silicate, calcium silicate, magnesium aluminometasilicate; phosphates, e.g. calcium monohydrogen phosphate; carbonates, e.g. calcium carbonate; and sulfuric acid salts such as calcium sulfate, can be mentioned), lubricants (for example, stearic acid, metal salts of stearic acid such as calcium stearate or magnesium stearate; talc; colloidal silica; waxes such as bee gum or spermaceti; boric acid; adipic acid; sulfates such as sodium sulfate; glycol; fumaric acid; sodium benzoate; DL leucine; sodium salt of fatty acid; lauryl sulfates such as sodium lauryl sulfate or magnesium lauryl sulfate; silicic acids such as silicic anhydride or silicate hydrate; and the aforementioned starch derivatives can be mentioned), binders (for example, hydroxypropyl cellulose, hydroxypropyl methyl cellulose, polyvinylpyrrolidone, macrogol and compounds similar to the aforementioned excipient can be mentioned), disintegrants (for example, cellulose derivatives such as low-substituted hydroxypropyl cellulose, carboxymethyl cellulose, calcium carboxymethyl cellulose or internally crosslinked sodium carboxymethyl cellulose; or chemically modified starches or celluloses such as carboxymethyl starch, sodium carboxymethyl starch or crosslinked polyvinylpyrrolidone can be mentioned), stabilizers (for example, esters of para-hydroxybenzoic acid such as methyl paraben or propyl paraben; alcohols such as chlorobutanol, benzyl alcohol or phenyl ethyl alcohol, benzalkonium chloride; phenols such as phenol or cresol; thimerosal; dehydroacetic acid; and sorbic acid can be mentioned) and corrigents for flavor and smell (for example, commonly used sweeteners, acidifiers or fragrances can be mentioned) or diluents.

The dosage amount varies to a large extent depending on conditions such as the activity of the drug, the symptoms, age, weight and the like of the patient (warm-blooded animal, especially human). For humans, it is desirable to administer (orally or by intravenous injection) a dosage of 0.0005 mg/kg to 50 mg/kg. Preferably the range is from 0.0005 mg/kg to 1 mg/kg, and more preferably from 0.001 mg/kg to 0.1 mg/kg, per dose. For warm-blooded animals other than human, for example, mouse, the dosage range is from 0.0005 mg/kg to 50 mg/kg, and preferably from 0.01 mg/kg to 10 mg/kg. The drug (dose) may be administered 1 to 6 times per day and preferably 1 to 2 times per day, depending on the symptoms.

In addition, the compound having PPARγ activation potency (preferably a compound represented by the general formula (I)) or a pharmacologically acceptable salt thereof, and the epidermal growth factor receptor (EGFR) inhibitor, the vascular endothelial growth factor receptor (VEGFR) inhibitor or the Raf kinase inhibitor can each be formulated alone in a separate administration form, or can be formulated into a physically uniform administration form by mixing them.

When each of such separate administration form or uniform administration form is used, each of the compound having PPARγ activation potency or a pharmacologically acceptable salt thereof, the epidermal growth factor receptor (EGFR) inhibitor, the vascular endothelial growth factor receptor (VEGFR) inhibitor and the Raf kinase inhibitor or a mixture with a pharmaceutically acceptable carrier, e.g., an excipient or diluent can be administered orally by a tablet, a capsule, granules, powders or syrup, or parenterally by injection or suppository.

These pharmaceutical preparations are prepared in accordance with a known process by using additives including excipients (for example, organic excipients such as sugar derivatives, e.g. lactose, sucrose, glucose, mannitol or sorbitol; starch derivatives, e.g. corn starch, potato starch, α-starch or dextrin; cellulose derivatives, e.g. crystalline cellulose; gum arabic; dextrane; or pullulan, and inorganic excipients such as silicate derivatives, e.g. light silicic anhydride, synthetic aluminum silicate, calcium silicate, magnesium aluminometasilicate; phosphates, e.g. calcium monohydrogenphosphate; carbonates, e.g. calcium carbonate; and sulfuric acid salts such as calcium sulfate, can be mentioned), lubricants (for example, stearic acid, metal salts of stearic acid such as calcium stearate or magnesium stearate; talc; colloidal silica; waxes such as beeswax or spermaceti; boric acid; adipic acid; sulfates such as sodium sulfate; glycol; fumaric acid; sodium benzoate; DL leucine; lauryl sulfates such as sodium lauryl sulfate or magnesium lauryl sulfate; silicic acids such as silicic anhydride or silicate hydrate; and the aforementioned starch derivatives can be mentioned), binders (for example, hydroxypropyl cellulose, hydroxypropyl methyl cellulose, polyvinylpyrrolidone, macrogol and compounds similar to the aforementioned excipient can be mentioned), disintegrants (for example, cellulose derivatives such as low-substituted hydroxypropyl cellulose, carboxymethyl cellulose, calcium carboxymethyl cellulose or internally crosslinked sodium carboxymethyl cellulose; or chemically modified starches or celluloses such as carboxymethyl starch, sodium carboxymethyl starch or crosslinked polyvinylpyrrolidone can be mentioned), emulsifiers (for example colloidal clays such as bentonite and bee gum; metal hydroxides such as magnesium hydroxide and aluminum hydroxide; anionic surfactants such as sodium lauryl sulfate and calcium stearate; cationic surfactants such as benzalkonium chloride; and, nonionic surfactants such as polyoxyethylene alkyl ether, polyoxyethylene sorbitan fatty acid ester, and sucrose fatty acid ester), stabilizers (for example, esters of para-hydroxybenzoic acid such as methyl paraben or propyl paraben; alcohols such as chlorobutanol, benzyl alcohol or phenyl ethyl alcohol; benzalkonium chloride; phenols such as phenol or cresol; thimerosal; dehydroacetic acid; and sorbic acid can be mentioned) and corrigents for flavor and smell (for example, commonly used sweeteners, acidifiers or fragrances can be mentioned) or diluents.

The administration ratio of the compound having PPARγ activation potency or a pharmacologically acceptable salt thereof, and the epidermal growth factor receptor (EGFR) inhibitor, the vascular endothelial growth factor receptor (VEGFR) inhibitor or the Raf kinase inhibitor may vary depending on various conditions such as the activity of the individual drugs, and symptoms, age, weight of the patient.

Although its dosage amount varies depending on the activity of individual drugs, and symptom, age, weight and the like of a patient (warm-blooded animal, especially human), in the case of oral administration for example, it is desirable to administer from 0.1 mg/kg to 100 mg/kg (preferably 0.1 mg/kg to 20 mg/kg) per dose, and in the case of intravenous injection, it is desirable to administer from 0.01 mg/kg to 100 mg/kg (preferably 0.1 mg/kg to 10 mg/kg) per dose, 1 to 6 times a day (preferably 1 to 2 times per day), depending on the symptom, at the same time or separately after some time.

Further, the ratio of (i) the compound having PPAR γ activation potency, and (ii) the epidermal growth factor receptor (EGFR) inhibitor, the vascular endothelial growth factor receptor (VEGFR) inhibitor or the Raf kinase inhibitor in a dose may vary to a large extent. However, the ratio of dosage amount of the (a) compound having PPARγ activation potency or a pharmacologically acceptable salt thereof, and (b) the epidermal growth factor receptor (EGFR) inhibitor, the vascular endothelial growth factor receptor (VEGFR) inhibitor or the Raf kinase inhibitor may be in the range of 1:1000 to 1000:1 (i.e., 1 to 0.001) in weight ratio, preferably the ratio is 1:1000 to 1:10 and more preferably 1:1000 to 1:100.

EXAMPLES

Hereinafter, the present invention will be described in more detail with reference to production examples, test examples and preparation examples; however, the scope of the present invention is not intended to be limited to these.

Production Example 1

5-(4-(6-(3-Isopropylamino-phenoxy)-1-methyl-1H-benzimidazol-2-ylmethoxy)-benzyl)-thiazolidine-2,4-dione.dihydrochloride A mixture of 0.74 g of N-(2-amino-5-(3-isopropylamino-phenoxy)-phenyl)-N-methylcarbamic acid t-butyl ester obtained in Reference Example 2, 0.70 g of 4-(2,4-dioxothiazolidin-5-ylmethyl)-phenoxyacetic acid (Japanese Patent Application (Kokai) No. Hei 11-193276), 0.41 g of diethyl cyanophosphonate, 0.25 g of triethylamine, and 30 ml of anhydrous tetrahydrofuran was stirred at room temperature for 4.5 hours. The reaction mixture was concentrated, followed by addition of water and extraction with ethyl acetate. After the extraction solution was dried over anhydrous sodium sulfate, the solvent was distilled off, and the resulting residue was purified by silica gel column chromatography (eluting solvent: ethyl acetate/n-hexane=2/3) to give N-(5-(3-isopropylamino-phenoxy)-2-(4-(2,4-dioxothiazolidin-5-ylmethyl)-phenoxyacetylamino)-phenyl)-N-methylcarbamic acid t-butyl ester as an intermediate. After this intermediate was dissolved in 50 ml of 4N hydrochloric acid/1,4-dioxane, the mixture was left to stand at room temperature for 16 hours, and the product which deposited was filtered and washed with ethyl acetate to give the title compound (0.76 g, 64% yield).

$^1$H-NMR (DMSO-d$_6$) δ: 1.21 (6H, d, J=6.4 Hz), 3.11 (1H, dd, J=14 and 9.0 Hz), 3.34 (1H, dd, J=14 and 4.4 Hz), 3.57-3.65 (1H, m), 3.95 (3H, s), 4.91 (1H, dd, J=9.0 and 4.4 Hz), 5.63 (2H, s), 6.70-7.20 (3H, m), 7.14 (2H, d, J=8.7 Hz), 7.25 (2H, d, J=8.7 Hz), 7.25 (1H, d, J=3.3 Hz), 7.35-7.45 (1H, m), 7.68 (1H, d, J=1.9 Hz), 7.83 (1H, d, J=8.9 Hz), 12.05 (1H, s; disappeared due to addition of deuterium oxide).

Production Example 2

5-(4-(6-(3-(Isobutyl-methyl-amino)-phenoxy)-1-methyl-1H-benzimidazol-2-ylmethoxy)-benzyl)-thiazolidine-2,4-dione.dihydrochloride N-(2-amino-5-(3-(isobutyl-methyl-amino)phenoxy)-phenyl)-N-methylcarbamic acid t-butyl ester obtained in Reference Example 5 was used in place of N-(2-amino-5-(3-isopropylamino-phenoxy)-phenyl)-N-methylcarbamic acid t-butyl ester of Production Example 1 to give the title compound in similar manner to Production Example 1.

$^1$H-NMR (DMSO-d$_6$) δ: 0.86 (6H, d, J=6.7 Hz), 1.90-1.99 (1H, m), 2.91 (3H, s), 3.08-3.14 (3H, m), 3.34 (1H, dd, J=14 and 4.4 Hz), 3.94 (3H, s), 4.91 (1H, dd, J=9.0 and 4.4 Hz), 5.65 (2H, s), 6.21 (1H, br), 6.39 (1H, br), 6.53 (1H, br), 7.15-7.27 (6H, m), 7.62 (1H, d, J=2.1 Hz), 7.80 (1H, d, J=8.9 Hz), 12.04 (1H, br; disappeared due to addition of deuterium oxide).

Production Example 3

5-(4-(6-(4-(Isobutyl-methyl-amino)-phenoxy)-1-methyl-1H-benzimidazol-2-ylmethoxy)-benzyl)-thiazolidine-2,4-dione.dihydrochloride N-(2-methyl-5-(4-(isobutyl-methyl-amino)phenoxy)-phenyl)methylamine obtained in Reference Example 8 was used in place of N-(2-amino-5-(3-isopropylamino-phenoxy)-phenyl)-N-methylcarbamic acid t-butyl ester of Production Example 1 to give the title compound in similar manner to Production Example 1.

$^1$H-NMR (DMSO-d$_6$) δ: 0.90 (6H, d, J=4.4 Hz), 1.75-2.05 (1H, m), 1.99 (3H, s), 2.90-3.10 (2H, m), 3.11 (1H, dd, J=14 and 8.9 Hz), 3.34 (1H, dd, J=14 and 4.4 Hz), 3.92 (3H, s), 4.91 (1H, dd, J=8.9 and 4.4 Hz), 5.62 (2H, s), 6.65-7.20 (5H, m), 7.13 (2H, d, J=8.7 Hz), 7.25 (2H, d, J=8.7 Hz), 7.45-7.60 (1H, m), 7.78 (1H, d, J=8.9 Hz), 12.05 (1H, s; disappeared by addition of deuterium oxide).

Production Example 4

5-(4-(6-(3-(Ethyl-isopropyl-amino)-phenoxy)-1-methyl-1H-benzimidazol-2-ylmethoxy)-benzyl)-thiazolidine-2,4-dione A mixture of 620 mg of 5-(4-(6-(3-isopropylamino-phenoxy)-1-methyl-1H-benzimidazol-2-ylmethoxy)-benzyl)-thiazolidine-2,4-dione.dihydrochloride obtained in Production Example 1, 66 mg of acetaldehyde, 90 mg of acetic acid, 318 mg of sodium triacetoxyborohydride and 15 ml of anhydrous tetrahydrofuran was stirred at room temperature for 1 hour. The reaction mixture was concentrated, followed by addition of water and extraction with ethyl acetate. After the extraction solution was dried over anhydrous sodium sulfate, the solvent was distilled off, and the resulting residue was purified by silica gel column chromatography (eluting solvent: ethyl acetate/n-hexane=1/1) to give the title compound (260 mg, 48% yield).

$^1$H-NMR (DMSO-d$_6$) δ: 1.06 (3H, t, J=7.0 Hz), 1.11 (6H, d, J=6.6 Hz), 3.05 (1H, dd, J=14 and 9.2 Hz), 3.18 (2H, q, J=7.0 Hz), 3.31 (1H, dd, J=14 and 4.3 Hz), 3.79 (3H, s), 3.94-4.04 (1H, m), 4.87 (1H, dd, J=9.2 and 4.3 Hz), 5.63 (2H, s), 6.11 (1H, dd, J=7.9 and 2.0 Hz), 6.34 (1H, t, J=2.2 Hz), 6.46 (1H, dd, J=8.5 and 2.3 Hz), 6.92 (1H, dd, J=8.8 and 2.2 Hz), 7.06-7.11 (3H, m), 7.19 (1H, d, J=8.7 Hz), 7.28 (1H, d, J=2.3 Hz), 7.63 (1H, d, J=8.7 Hz), 12.02 (1H, s; disappeared due to addition of deuterium oxide).

Production Example 5

5-(4-(6-(4-Isopropylamino-phenoxy)-1-methyl-1H-benzimidazol-2-ylmethoxy)-benzyl)-thiazolidine-2,4-dione 5-(4-(6-(4-Amino-phenoxy)-1-methyl-1H-benzimidazol-2-ylmethoxy)-benzyl)-thiazolidine-2,4-dione.dihydrochloride (Japanese Patent Application (Kokai) No. Hei 11-193276) was used in place of 5-(4-(6-(3-isopropylamino-phenoxy)-1-methyl-1H-benzimidazol-2-ylmethoxy)-benzyl)-thiazolidine-2,4-dione.dihydrochloride of Production Example 4, and acetone was used in place of acetaldehyde to give the title compound in similar manner to Production Example 4.

$^1$H-NMR (DMSO-$d_6$) δ: 1.13 (6H, d, J=6.3 Hz), 3.05 (1H, dd, J=14 and 9.1 Hz), 3.31 (1H, dd, J=14 and 4.3 Hz), 3.45-3.52 (1H, m), 3.75 (3H, s), 4.87 (1H, dd, J=9.1 and 4.3 Hz), 5.24 (1H, br; disappeared due to addition of deuterium oxide), 5.34 (2H, s), 6.56 (2H, dd, J=12 and 3.3 Hz), 6.81 (2H, d, J=8.6 Hz), 6.83 (1H, dd, J=8.2 and 2.3 Hz), 7.04-7.07 (3H, m), 7.19 (2H, d, J=8.6 Hz), 7.57 (1H, d, J=8.8 Hz), 12.02 (1H, br; disappeared due to addition of deuterium oxide).

Production Example 6

5-(4-(6-(4-sec-Butylamino-phenoxy)-1-methyl-1H-benzimidazol-2-ylmethoxy)-benzyl)-thiazolidine-2,4-dione 5-(4-(6-(4-Amino-phenoxy)-1-methyl-1H-benzimidazol-2-ylmethoxy)-benzyl)-thiazolidine-2,4-dione.dihydrochloride was used in place of 5-(4-(6-(3-isopropylamino-phenoxy)-1-methyl-1H-benzimidazol-2-ylmethoxy)-benzyl)-thiazolidine-2,4-dione.dihydrochloride of Production Example 4, and methyl ethyl ketone was used in place of acetaldehyde to give the title compound in similar manner to Production Example 4.

$^1$H-NMR (DMSO-$d_6$) δ: 0.90 (3H, t, J=7.4 Hz), 2.17 (3H, d, J=6.4 Hz), 1.34-1.46 (1H, m), 1.48-1.59 (1H, m), 3.06 (1H, dd, J=14 and 9.2 Hz), 3.24-3.34 (2H, m), 3.75 (3H, s), 4.87 (1H, dd, J=9.2 and 4.3 Hz), 5.23 (1H, br; disappeared due to addition of deuterium oxide), 5.34 (2H, s), 6.57 (2H, d, J=8.7 Hz), 6.81 (2H, d, J=8.9 Hz), 6.84 (1H, dd, J=8.8 and 2.2 Hz), 7.01-7.09 (3H, m), 7.19 (2H, d, J=8.7 Hz), 7.57 (1H, d, J=8.8 Hz), 12.01 (1H, br; disappeared due to addition of deuterium oxide).

Production Example 7

5-(4-(6-(4-Isobutylamino-phenoxy)-1-methyl-1H-benzimidazol-2-ylmethoxy)-benzyl)-thiazolidine-2,4-dione 5-(4-(6-(4-Amino-phenoxy)-1-methyl-1H-benzimidazol-2-ylmethoxy)-benzyl)-thiazolidine-2,4-dione.dihydrochloride was used in place of 5-(4-(6-(3-isopropylamino-phenoxy)-1-methyl-1H-benzimidazol-2-ylmethoxy)-benzyl)-thiazolidine-2,4-dione.dihydrochloride of Production Example 4, and isobutyl aldehyde was used in place of acetaldehyde to give the title compound in similar manner to Production Example 4.

$^1$H-NMR (DMSO-$d_6$) δ: 0.94 (6H, d, J=6.7 Hz), 1.77-1.88 (1H, m), 2.78-2.81 (2H, m), 3.05 (1H, dd, J=14 and 9.3 Hz), 3.31 (1H, dd, J=14 and 4.3 Hz), 3.74 (3H, s), 4.86 (1H, dd, J=9.3 and 4.3 Hz), 5.34 (2H, s), 5.50 (1H, s; disappeared due to addition of deuterium oxide), 6.57 (2H, dd, J=6.8 and 2.0 Hz), 6.81 (2H, d, J=8.8 Hz), 6.83 (1H, dd, J=8.6 and 2.4 Hz), 7.04-7.07 (3H, m), 7.19 (2H, d, J=8.6 Hz), 7.56 (1H, d, J=8.8 Hz), 12.01 (1H, s; disappeared due to addition of deuterium oxide).

Production Example 8

5-(4-(6-(4-Amino-3,5-dimethyl-phenoxy)-1-methyl-1H-benzimidazol-2-ylmethoxy)-benzyl)-thiazolidine-2,4-dione.dihydrochloride N-(2-Amino-5-(4-t-butoxycarbonylamino-3,5-dimethyl-phenoxy)-phenyl)-N-methylcarbamic acid t-butyl ester obtained in Reference Example 11 was used in place of N-(2-amino-5-(3-isopropylamino-phenoxy)-phenyl)-N-methylcarbamic acid t-butyl ester of Production Example 1 to give the title compound in similar manner to Production Example 1.

$^1$H-NMR (DMSO-$d_6$) δ: 2.34 (6H, s), 3.10 (1H, dd, J=14 and 9.0 Hz), 3.34 (1H, dd, J=14 and 4.4 Hz), 3.93 (3H, s), 4.91 (1H, dd, J=4.4 and 9.0 Hz), 5.62 (2H, s), 6.80 (2H, s), 7.14 (2H, d, J=8.7 Hz), 7.18 (1H, dd, J=8.9 and 2.2 Hz), 7.25 (2H, d, J=8.7 Hz), 7.61 (1H, d, J=2.2 Hz), 7.81 (1H, d, J=8.9 Hz), 12.1 (1H, br; disappeared due to addition of deuterium oxide).

Reference Example 1

N-(5-(3-Aminophenoxy)-2-nitrophenyl)-N-methylcarbamic acid t-butyl ester

To a 80 ml of anhydrous N,N-dimethylformamide suspension containing 2.18 g of sodium hydride (55 wt %) was added 5.45 g of 3-aminophenol, and the mixture was stirred at room temperature for 20 minutes. Subsequently, 14.3 g of N-(5-chloro-2-nitrophenyl)-N-methylcarbamic acid t-butyl ester (Japanese Patent Application (Kokai) No. Hei 11-193276) was added in small amounts, and the mixture was stirred at 100° C. for 6 hours. The reaction mixture was concentrated, followed by addition of water and neutralization using 3N hydrochloric acid and sodium bicarbonate powder. The insoluble product which deposited was filtered, washed with water, and then dried under reduced pressure to give the title compound (16.6 g, 92% yield).

$^1$H-NMR (DMSO-$d_6$) δ: 1.23 and 1.42 (9H in total, s each), 3.18 (3H, s), 5.38 (2H, s; disappeared due to addition of deuterium oxide), 6.25 (1H, dd, J=7.6 and 2.4 Hz), 6.31 (1H, s), 6.46 (1H, dd, J=8.1 and 1.0 Hz), 6.88 (1H, dd, J=9.0 and 2.1 Hz), 7.09 (1H, t, J=8.0 Hz), 7.16 (1H, s), 8.00 (1H, d, J=9.0 Hz).

Reference Example 2

N-(2-Amino-5-(3-isopropylamino-phenoxy)-phenyl)-N-methylcarbamic acid t-butyl ester A mixture of 14.4 g of N-(5-(3-aminophenoxy)-2-nitrophenyl)-N-methylcarbamic acid t-butyl ester, 2.90 g of acetone, 3.00 g of acetic acid, 10.6 g of sodium triacetoxyborohydride and 200 ml of anhydrous tetrahydrofuran was stirred at room temperature for 4 days. The reaction mixture was concentrated, followed by addition of water and extraction with ethyl acetate. After the extraction solution was dried over anhydrous sodium sulfate, the solvent was distilled off, and the resulting residue was purified by silica gel column chromatography (eluting solvent: ethyl acetate/n-hexane=2/3) to give N-(5-(3-isopropylamino-phenoxy)-2-nitrophenyl)-N-methylcarbamic acid t-butyl ester, as an intermediate. This intermediate was dissolved in 200 ml of methanol, followed by addition of 2.02 g of 10% palladium-carbon, and the mixture was vigorously stirred under a hydrogen atmosphere at room temperature for 2.5 hours. After completion of the reaction, the catalyst was filtered, and the solvent was distilled off to give the title compound (12.0 g, 81% yield).

$^1$H-NMR (DMSO-$d_6$) δ: 1.08 (6H, d, J=6.4 Hz), 1.29 (9H, s), 2.98 (3H, s), 3.40-3.47 (1H, m), 4.78 (2H, s; disappeared due to addition of deuterium oxide), 5.45 (1H, d, J=7.8 Hz; disappeared due to addition of deuterium oxide), 5.96 (1H, d, J=7.2 Hz), 6.07 (1H, t, J=2.2 Hz), 6.20 (1H, dd, J=8.1 and 1.9 Hz), 6.60 (1H, s), 6.71 (2H, s), 6.93 (1H, t, J=8.1 Hz).

Reference Example 3

N-(5-(3-Bromophenoxy)-2-nitrophenyl)-N-methylcarbamic acid t-butyl ester

To a 50 ml of anhydrous N,N-dimethylformamide suspension containing 2.5 g of sodium hydride (55% weight) was added 10.0 g of 3-bromophenol, and the mixture was stirred under ice-cooling for 15 minutes. Subsequently, a solution of 16.6 g of N-(5-chloro-2-nitrophenyl)-N-methylcarbamic acid t-butyl ester dissolved in 70 ml of anhydrous N,N-dimethylformamide was added to the mixture in drops, and the mixture was stirred at 100° C. for 3 hours. The reaction mixture was concentrated, followed by addition of water, neutralization using 3N hydrochloric acid and extraction with ethyl acetate. The extraction solution was washed with saturated saline, and then dried over anhydrous sodium sulfate. Ethyl acetate was distilled off from the extraction solution, and the insoluble product which deposited was washed with hexane and filtered, followed by drying under reduced pressure, to give the title compound (20.2 g, 83% yield).

$^1$H-NMR (CDCl$_3$) δ: 1.24 (9H, s), 3.19 (3H, s), 6.97 (1H, dd, J=9.0 and 2.4 Hz), 7.22 (1H, d, J=7.9 Hz), 7.29 (1H, d, J=1.7 Hz), 7.42-7.51 (3H, m), 8.03 (1H, d, J=9.0 Hz).

Reference Example 4

N-(5-(3-(Isobutyl-methyl-amino)phenoxy)-2-nitrophenyl)-N-methylcarbamic acid t-butyl ester 700.0 mg of N-(5-(3-bromophenoxy)-2-nitrophenyl)-N-methylcarbamic acid t-butyl ester obtained in Reference Example 3, 0.24 ml of isobutylmethylamine, 151.0 mg of tris(dibenzylideneacetone)dipalladium, 115.7 mg of 2-(dicyclohexylphosphino)biphenyl and 277.7 mg of potassium t-butoxide were suspended in 4 ml of anhydrous toluene, and the mixture was stirred at 100° C. for 1.5 hours. Water was added to the reaction mixture, followed by extraction with ethyl acetate. After the extracted solution was washed with saturated saline and dried over anhydrous sodium sulfate, the solvent was distilled off, and the resulting residue was purified by silica gel column chromatography (eluting solvent: ethyl acetate/n-hexane=1/7) to give the title compound (204.2 mg, 29% yield).

$^1$H-NMR (CDCl$_3$) δ: 0.80 (6H, d, J=6.6 Hz), 1.25 (9H, s), 1.88-2.01 (1H, m), 2.85 (3H, s), 2.95 (2H, d, J=7.3 Hz), 3.14 (3H, s), 6.20-6.27 (2H, m), 6.43 (1H, dd, J=8.8 and 2.2 Hz), 6.72-6.83 (2H, m), 7.11 (1H, t, J=8.1 Hz), 7.81 (1H, d, J=9.5 Hz).

Reference Example 5

N-(2-Amino-5-(3-(isobutyl-methyl-amino)phenoxy)-phenyl)-N-methylcarbamic acid t-butyl ester 204.2 mg of N-(5-(3-(isobutyl-methyl-amino)phenoxy)-2-nitrophenyl)-N-methylcarbamic acid t-butyl ester obtained in Reference Example 4 was dissolved in 10 ml of ethanol, followed by addition of 100.0 mg of 10% palladium-carbon, and the mixture was stirred vigorously under a hydrogen atmosphere at room temperature for 2.5 hours. After completion of the reaction, the catalyst was filtered, and the solvent was distilled off. The resulting residue was purified by silica gel column chromatography (eluting solvent: ethyl acetate/n-hexane=1/4→1/3) to give the title compound (145.4 mg, 77% yield).

$^1$H-NMR (CDCl$_3$) δ: 0.90 (6H, d, J=6.6 Hz), 1.57 (9H, s), 1.98-2.09 (1H, m), 2.92 (3H, s), 3.06 (2H, d, J=7.3 Hz), 3.13 (3H, s), 3.64 (2H, s; lost due to addition of deuterium oxide), 6.30 (1H, t, J=2.2 Hz), 6.35 (1H, dd, J=8.1 and 2.2 Hz), 6.70-6.88 (3H, m), 7.08 (1H, t, J=8.2 Hz), 7.25-7.31 (1H, m).

Reference Example 6

(4-(Isobutyl-methyl-amino)phenoxy)-t-butyldimethylsilane 5 ml of (4-bromophenoxy)-t-butyldimethylsilane, 2.9 ml of isobutylmethylamine, 458.0 mg of palladium acetate, 1.2 g of 2-(di t-butylphosphino)biphenyl and 2.9 g of sodium t-butoxide were suspended in 40 ml of anhydrous toluene, and the mixture was stirred at 100° C. for 1.5 hours. The catalyst was filtered, followed by addition of water and extraction with ethyl acetate. After the extraction solution was washed with saturated saline and dried over anhydrous sodium sulfate, the solvent was distilled off, and the resulting residue was purified by silica gel column chromatography (eluting solvent: ethyl acetate/n-hexane=1/40→1/20) to give the title compound (3.83 g, 64% yield).

$^1$H-NMR (CDCl$_3$) δ: 0.16 (6H, s), 0.91 (6H, d, J=6.6 Hz), 0.97 (9H, s), 1.94-2.05 (1H, m), 2.87 (3H, s), 2.98 (2H, d, J=7.3 Hz), 6.57 (2H, d, J=8.8 Hz), 6.72 (2H, d, J=8.8 Hz).

Reference Example 7

N-(5-(4-(Isobutyl-methyl-amino)phenoxy)-2-nitrophenyl)methylamine 3.83 g of (4-(isobutyl-methyl-amino)phenoxy)-t-butyldimethylsilane obtained in Reference Example 6 was dissolved in 20 ml of anhydrous tetrahydrofuran, followed by addition of 20 ml of 1M tetra-n-butylammonium fluoride tetrahydrofuran solution, and the mixture was stirred at room temperature for 30 minutes. The reaction mixture was concentrated, followed by addition of water and extraction with ethyl acetate. After the extraction solution was washed with saturated saline and dried over anhydrous sodium sulfate, the solvent was distilled off, and the resulting residue was purified by silica gel column chromatography (eluting solvent: ethyl acetate/n-hexane=1/5). The resulting product was dissolved in 4N hydrochloric acid-1,4-dioxane, and the mixture was stirred at room temperature for 30 minutes. The reaction liquid was concentrated and washed with diethyl ether to give 4-isobutylmethylaminophenol.monohydrochloride, which is an intermediate. 20 ml of anhydrous N,N-dimethylformamide suspension containing 500.0 mg of this intermediate and 2.6 g of potassium carbonate was stirred at room temperature for 15 minutes. Subsequently, 664.7 mg of N-(5-chloro-2-nitrophenyl)-N-methylcarbamic acid t-butyl ester was added to the mixture, and the mixture was stirred at 150° C. for 3 hours. The reaction mixture was concentrated, followed by addition of water and extraction with ethyl acetate. After the extraction solution was washed with saturated saline and dried over anhydrous sodium sulfate, the solvent was distilled off, and the resulting residue was purified by silica gel column chromatography (eluting solvent: ethyl acetate/toluene=1/30) to give the title compound (256.1 mg, 34% yield).

$^1$H-NMR (CDCl$_3$) δ: 0.96 (6H, d, J=6.8 Hz), 2.00-2.13 (1H, m), 2.92 (3H, d, J=5.9 Hz), 2.98 (3H, s), 3.12 (2H, d, J=7.8 Hz), 6.19-6.23 (2H, m), 6.68 (2H, d, J=8.8 Hz), 6.96 (2H, d, J=8.8 Hz), 8.13 (1H, d, J=9.8 Hz).

Reference Example 8

N-(2-Methyl-5-(4-(isobutyl-methyl-amino)phenoxy)-phenyl)methylamine

N-(5-(4-(isobutyl-methyl-amino)phenoxy)-2-nitrophenyl)methylamine obtained in Reference Example 7 was used in place of N-(5-(3-(isobutyl-methyl-amino)phenoxy)-2-nitrophenyl)-N-methylcarbamic acid t-butyl ester of Reference Example 5 to give the title compound in similar manner to Reference Example 5.

$^1$H-NMR (CDCl$_3$) δ: 0.88 (6H, d, J=6.6 Hz), 1.94-2.04 (1H, m), 2.77 (3H, s), 2.87 (3H, s), 2.99 (2H, d, J=7.3 Hz), 3.22 (2H, s), 6.16 (1H, dd, J=8.1 and 2.5 Hz), 6.33 (1H, d, J=2.5 Hz), 6.57 (1H, d, J=8.1 Hz), 6.59 (2H, d, J=8.8 Hz), 6.87 (2H, d, J=8.8 Hz).

Reference Example 9

N-(5-(4-Amino-3,5-dimethylphenoxy)-2-nitrophenyl)-N-methylcarbamic acid t-butyl ester 4-Amino-3,5-dimethylphenol was used in place of 3-aminophenol of Reference Example 1 and the same treatment was carried out in similar manner to Reference Example 1, followed by purification by silica gel column chromatography (eluting solvent: ethyl acetate/n-hexane=1/2) to give the title compound.

$^1$H-NMR (DMSO-d$_6$) δ: 1.23 and 1.41 (total 9H, s each), 2.10 (6H, s), 3.17 (3H, s), 4.66 (2H, br; disappeared due to addition of deuterium oxide), 6.69 (2H, s), 6.75 (1H, dd, J=9.1 and 2.5 Hz), 7.07 (1H, s), 7.96 (1H, d, J=9.1).

Reference Example 10

N-(5-(4-t-Butoxycarbonylamino-3,5-dimethylphenoxy)-2-nitrophenyl)-N-methylcarbamic acid t-butyl ester A mixture of 2.27 g of N-(5-(4-amino-3,5-dimethylphenoxy)-2-nitrophenyl)-N-methylcarbamic acid t-butyl ester, 1.28 g of di-t-butyl bicarbonate, 0.59 g of triethylamine and 20 ml of anhydrous tetrahydrofuran was heated under reflux for 6 hours. The reaction mixture was concentrated, followed by addition of water and extraction with ethyl acetate. After the extraction solution was dried over anhydrous sodium sulfate, the solvent was distilled off, and the resulting residue was purified by silica gel column chromatography (eluting solvent: ethyl acetate/n-hexane=1/10) to give the title compound (1.74 g, 61% yield).

$^1$H-NMR (DMSO-d$_6$) δ: 1.24 and 1.42 (total 9H, s each), 1.46 (9H, s), 2.17 (6H, s), 3.19 (3H, s), 6.84 (1H, dd, J=9.0 and 2.7), 6.90 (2H, s), 7.21 (1H, s), 8.00 (1H, d, J=9.0), 8.42 (1H, s; disappeared due to addition of deuterium oxide).

Reference Example 11

N-(2-Amino-5-(4-t-butoxycarbonylamino-3,5-dimethyl-phenoxy)-phenyl)-N-methylcarbamic acid t-butyl ester N-(5-(4-t-butoxycarbonylamino-3,5-dimethylphenoxy)-2-nitrophenyl)-N-methylcarbamic acid t-butyl ester obtained in Reference Example 10 was used in place of N-(5-(3-(isobutyl-methyl-amino)phenoxy)-2-nitrophenyl)-N-methylcarbamic acid t-butyl ester of Reference Example 5, and the process was carried out analogously to Reference Example 5, followed by purification by silica gel column chromatography (elution solvent: ethyl acetate/n-hexane=1/2) to give the title compound.

$^1$H-NMR (DMSO-d$_6$) δ: 1.30 and 1.37 (total 9H, s each), 1.44 (9H, s), 2.07 (6H, s), 2.98 (3H, s), 4.83 (2H, br; disappeared due to addition of deuterium oxide), 6.54 (2H, s), 6.58-6.74 (3H, m), 8.22 (1H, s; disappeared due to addition of deuterium oxide).

Test Example 1

Evaluation of Cancer Cell Proliferation Inhibitory Activity

Human gastric cancer cell line (MKN74, MKN28) purchased from Immuno-Biological Laboratories Co., Ltd., human breast cancer cell line (ZR-75-1), small-cell lung cancer line (SBC-1), pancreatic cancer cell line (AsPC-1), prostate cancer cell line (DU-145), kidney cancer cell line (ACHN), medulloblastoma line (D341 Med), human sarcoma cell line (rhabdomyosarcoma line A-204, Ewing's sarcoma line RD-ES, liposarcoma line SW872) and multiple myeloma line (U266) that were purchased from American Tissue Culture Collection were used in the test. MKN74, MKN28, ZR-75-1, SBC-1 and AsPC-1 were cultivated using 10% fetal bovine serum (Hyclone Laboratories, Inc.,)-RPMI (Invitrogen Corporation), RD-ES using 15% fetal bovine serum (Hyclone Laboratories, Inc.)-RPMI (Invitrogen Corporation), D341 Med using 10% fetal bovine serum (Hyclone Laboratories, Inc.)-MEMα (Invitrogen Corporation), ACHN using 10% fetal bovine serum (Hyclone Laboratories, Inc.)-E-MEM (Invitrogen Corporation), SW872 using 10% fetal bovine serum (Hyclone Laboratories, Inc.)-L15 (Invitrogen Corporation), A-204 using 10% fetal bovine serum (Hyclone Laboratories, Inc.)-McCoy's 5A (Invitrogen Corporation), and U266 using 0.5% fetal bovine serum (Hyclone Laboratories, Inc.)-2 ng/mL IL-6 (Genzyme Corporation)-RPMI (Invitrogen Corporation).

The cells were each inoculated on a 96-well plate for cell cultivation (Nalge Nunc International K.K.) at 1000 to 10000 cells/well, and at the same time, the compound of Production Example 8 having PPARγ activating action (hereinafter referred to as Compound X, and in FIGS. 1, 2 and 3 expressed as Compound X) dissolved in dimethyl sulfoxide (DMSO: Dojindo Laboratories) was added to each well so that the concentration of DMSO was 0.1% and the concentration of Compound X was 0.1, 1, or 10 μM (in the case of AsPC-1, 0.05, 0.5 or 5 μM). To the control group was added only DMSO so that its concentration became 0.1%. Then, the plate for cell cultivation was cultivated in the presence of 5% carbon dioxide at 37° C. for 7 days. Here, in the case of the U266 cells, cultivation was carried out for 4 days. After completion of the cultivation, 50% trichloroacetic acid (Wako Pure Chemical Industries, Ltd.) solution was added to the cell cultivation solution so that its final concentration became 10%, and the plate was left to stand at 4° C. for 1 hour to allow immobilization of the cells. Subsequently, each well was washed with distilled water 5 times, followed by adding 100 µL of 0.4% sulforhodamine B (Molecular Probes)-1% acetic acid solution to each of the wells and leaving them to stand for 30 minutes, thus staining the cells. Then, each well was washed with a 1% acetic acid solution 5 times and was air-dried. 10 mM Tris was added at 150 mL/well to each well in which cancer cells were immobilized and stained, and absorbance A490 of each well was measured using MICRO-PLATE READER Model 3550 (Bio-Rad Laboratories, Inc.). The average absorbance of each of the groups, which had been treated with respective concentration of the Compound X, was presented as a percentage expression, by taking the average absorbance of the control group, which had been treated with DMSO, as 100%. Accordingly, the cancer cell proliferation inhibitory activity of Compound X was considered.

The results are shown in FIGS. 1, 2 and 3. In each of the graphs, the longitudinal axis represents the absorbance [%], and the horizontal axis represents the concentration of Compound X [µM].

As seen in FIGS. 1, 2 and 3, Compound X showed significant proliferation inhibitory activity to all of the cancer cells. Accordingly, the possibility that Compound X possesses anticancer activity against human gastric cancer cell, human breast cancer cell, small cell lung cancer, pancreatic cancer cell, prostate cancer cell, kidney cancer cell, medulloblastoma, human sarcoma cell (rhabdomyosarcoma, Ewing's sarcoma and liposarcoma), and multiple myeloma, was strongly suggested.

Test Example 2

Evaluation of Cell Proliferation Inhibitory Activity Against Human Leukemia Cell Cell proliferation inhibitory effects against human leukemia cell with respect to the compound described in Production Example 8 having PPARγ activating action (hereinafter referred to as Compound X) was studied by using human leukemia cell lines HL-60 and THP-1 that were purchased from American Tissue Culture Collection. These cells were cultured using 10% fetal bovine serum (Hyclone Laboratories, Inc.)-RPMI (Invitrogen Corporation). HL-60 cells and THP-1 cells were inoculated on a 96-well plate at $2\times10^3$ cells/well, and at the same time, the agents at various concentrations dissolved in DMSO was added so that the concentration of DMSO became 0.1%. The concentration of Compound X was studied at 10, 25 and 50 µM (n=4). After the addition of the agent, cultivation was conducted in the presence of 5% carbon dioxide at 37° C. for 5 days. Then, Cell Titer 96 Aqueous One Solution Reagent (Promega Corp.) was added at 40 µl/well each, followed by 2 hours of cultivation. Absorbance A490 of each well was measured using MICRO-PLATE READER Model 3550 (Bio-Rad Laboratories, Inc.). The average absorbance of each of the groups, which had been treated with respective concentrations of Compound X, was presented as a percentage expression, by taking the average absorbance of the control group, which had been treated with DMSO, as 100%. Accordingly, the cancer cell proliferation inhibitory activity of Compound X was studied by subtracting this value from 100%.

The results are shown in Table 1.

TABLE 1

| Concentration of Compound X [µM] | HL-60 Proliferation inhibition rate % | THP-1 Proliferation inhibition rate % |
|---|---|---|
| 10 | 23 | 7 |
| 25 | 27* | 20 |
| 50 | 45** | 48** |

*P < 0.05,
**P < 0.01 (against agent non-addition group, Students' t test)

From the results in Table 1, it was shown that Compound X significantly inhibits proliferation activity of human leukemia cells.

Test Example 3

Evaluation of In Vivo Anti-Tumor Activity Against Human Colon Cancer Cells

In vivo anti-tumor activity against human colon cancer cells by the compound described in Production Example 8 having PPARγ activating action (hereinafter referred to as Compound X) and the compound described in Production Example 1 having PPARδ activating action (hereinafter referred to as Compound Y) was studied. In the experiment, human colon cancer line WiDr (purchased from American Type Culture Collection), in which it was confirmed that no mouse pathogenic microorganism was detected by quarantine, was transplanted to a subcutaneous axillary portion of a nude mouse BALB/cA Jcl-nu (CLEA Japan, Inc.), to subculture a tumor. The tumor was cut into small pieces of 5 mm size, and was transplanted to a right subcutaneous axillary portion of a BALB/cA Jcl-nu mouse by using a troker (CLEA Japan, Inc.). The required amounts of Compounds X and Y were each weighed and were dissolved in N,N-dimethylacetamide (DMA: Wako Pure Chemical Industries, Ltd.), and 5% Emulphor 620 (GAF Corporation)-saline (Otsuka Pharmaceutical Co., Ltd.) was then added to the mixtures in small amounts, so that the concentrations of the compounds were each adjusted to 0.2, 1 or 5 mg/mL. Here, DMA was made to have a final concentration of 2.5%. Each of these compound administration solutions was administered orally to a WiDr tumor-bearing nude mouse using a sonde (Fuchigami Kikaiten) from the day after transplantation of the tumor, once a day, 5 times per week, until 32 days after transplantation, in the amount of 0.1 mL per 10 g of mouse weight. Twice a week, the major axis and the minor axis of the transplanted tumor were measured using digital micrometer calipers (MAX-CAL MAX-15: Nihon Sokutei Kougu Kabusiki Kaisha), and tumor proliferation inhibitory activity was obtained from the following calculation formula and expressed as the tumor volume inhibition rate.

$$\text{Average tumor volume in each test group (mm}^3\text{)} = \tfrac{1}{2} \times (\text{minor axis})^2 \text{ (mm}^2\text{)} \times (\text{major axis}) \text{ (mm)}$$

$$\text{Tumor volume inhibition rate (\%)} = \{1 - (\text{average tumor volume of drug administration group/average tumor volume of drug non-administration group})\} \times 100$$

Evaluation of anti-tumor activity of each of the drug administration groups was determined by the tumor volume inhibition rate. In addition, a statistical difference test was determined by conducting Students' t test with respect to the tumor the volume of drug non-administration control group and the drug administration group 38 days after transplantation. Here, it was determined that there is a significant difference between the two groups when the p value is less than 0.05.

The results are shown in Table 2.

TABLE 2

| Compound | Administration amount [mg/kg] | Tumor volume inhibition rate (%)[a] | |
|---|---|---|---|
| | | Exp. 1 | Exp. 2 |
| Compound X | 50 | 49* | 38* |
| | 10 | N.D.[b] | 35* |
| | 2 | N.D. | 31* |
| Compound Y | 50 | 35* | 40* |
| | 10 | N.D. | 32* |
| | 2 | N.D. | 26* |

[a]WiDr, determined on Day 35
[b]N.D.; not done
*b < 0.01

From the results shown in Table 2, it became apparent that Compounds X and Y both show significant in vivo anti-tumor activity against human colon cancer line.

Test Example 4

Evaluation of In Vitro Cell Proliferation Inhibitory Activity Against Human Non-Small-Cell Lung Cancer Line by Combination Administration of a Compound Having PPARγ Activating Action and an Epidermal Growth Factor Receptor (EGFR) Inhibitor Effects of combined administration of the compound described in Production Example 8 having PPARγ activating action (hereinafter referred to as Compound X) and an epidermal growth factor receptor (EGFR) inhibitor against human non-small-cell lung cancer line A549 were studied by using in vitro cell proliferation inhibitory activity as an indicator.

Human non-small-cell lung cancer line A549 cells (purchased from American Tissue Culture Collection) were cultured using 10% fetal bovine serum (Hyclone Laboratories, Inc.)-RPMI (Invitrogen Corporation). A549 cells were inoculated on a 96-well plate at $5 \times 10^2$ cells/well, and at the same time, the agents of various concentrations dissolved in DMSO were added so that the concentration of DMSO became 0.1%. Compound X was studied with a concentration of 10 μM, and gefitinib (synthesized by Sankyo Company, Limited), as the EGFR inhibitor, with two concentrations of 0.1 and 0.5 μM (n=4). After the addition of the drugs, cells were cultivated in the presence of 5% carbon dioxide at 37° C. for 7 days. Then, Cell Titer 96 Aqueous One Solution Reagent (Promega Corp.) was added at 40 μl/well each, followed by 2 hours of cultivation. Absorbance A490 of each well was measured using MICROPLATE READER (Bio-Rad Laboratories, Inc.). The average absorbance of each of the groups, which had been treated with Compound X and gefitinib with respective concentrations, was presented as a percentage expression, by taking the average absorbance of the compound non-added control group (treated with DMSO only) as 100%. Accordingly, the cancer cell proliferation inhibitory action of Compound X, gefitinib, and a combination of these were considered by subtracting this value from 100%.

The results are shown in Table 3.

TABLE 3

| | Compound concentration | | | | | |
|---|---|---|---|---|---|---|
| Compound X [μM] | 0 | 0 | 0 | 10 | 10 | 10 |
| Gefitinib [μM] | 0 | 0.1 | 0.5 | 0 | 0.1 | 0.5 |
| Cell proliferation inhibition rate [%] | 0 | 5 | 22 | 12 | 37* | 50* |

*P < 0.05, (combined administration group versus each of single-drug treated group, Students' t test)

As shown in Table 3, the single-drug treatment with Compound X (10 μM) showed a proliferation inhibition rate of 12%, and the single-drug treatment with gefitinib (0.5 μM) showed a proliferation inhibition rate of 22%; however, the combined administration of both drugs showed a proliferation inhibition rate of 50%. From these results, it became apparent that the combined administration of Compound X and the epidermal growth factor receptor (EGFR) inhibitor shows synergistic cancer cell proliferation inhibitory activity.

Test Example 5

Evaluation of In Vivo Anti-Tumor Activity Against Non-Small-Cell Lung Cancer

In vivo anti-tumor activity against non-small-cell lung cancer of the compound described in Production Example 8 (hereinafter referred to as Compound X) was studied.

In the experiment, human non-small-cell lung cancer line A549 (purchased from American Type Culture Collection), in which it was confirmed that no mouse pathogenic microorganism was detected by quarantine, was transplanted to a subcutaneous axillary portion of a nude mouse BALB/cA Jcl-nu (CLEA Japan, Inc.), to subculture a tumor. The tumor was cut into small pieces of 5 mm size, and transplanted to a right subcutaneous axillary portion of a BALB/cA Jcl-nu mouse by using a troker (CLEA Japan, Inc.). Required amounts of Compound X and gefitinib (synthesized by Sankyo Company, Limited) as the EGFR inhibitor were each weighed, and solutions were prepared by suspending the compound described in Production Example 8 which has PPARγ activating action (hereinafter referred to as Compound X) in a 0.5%-methyl cellulose solution to have a final concentration of 1 mg/mL, and gefitinib in 0.05% Tween 80 (Tokyo Chemical Industry Co., Ltd.) to have a final concentration of 10 mg/mL. Each of these compound administration solutions was administered orally to a A549 tumor-bearing nude mouse using a sonde (Fuchigami Kikaiten) from 14 days after transplantation of the tumor, once a day, 5 times per week, until 60 days after transplantation, in the amount of 0.1 mL per 10 g of mouse weight. Twice a week, the major axis and the minor axis of the transplanted tumor were measured using digital micrometer calipers (MAX-CAL MAX-15: Nihon Sokutei Kougu Kabusiki Kaisha), and tumor proliferation inhibitory activity was obtained from the following calculation formula and expressed as the tumor volume inhibition rate.

The average tumor volume in each test group $(mm^3) = \frac{1}{2} \times (minor\ axis)^2\ (mm^2) \times (major\ axis)\ (mm)$ Tumor volume inhibition rate (%) = {1−(average tumor volume of drug administration group/average tumor volume of drug non-administration group)} × 100

Evaluation of anti-tumor activity for each of the drug administration groups was determined by the tumor volume inhibition rate. In addition, a statistical difference test was determined by conducting Students' t test with respect to tumor volume of the drug non-administration control group and the drug administration group 63 days after transplantation. Here, it was determined that there is a significant difference between the two groups when the p value is less than 0.05.

The results are shown in FIG. 4.

As shown in FIG. 4, Compound X showed significant anti-tumor activity by a tumor volume inhibition rate of 33%. In addition, gefitinib also showed significant anti-tumor activity by a tumor volume inhibition rate of 56%. On the other hand, when Compound X and gefitinib were administered in combination, enhancement in anti-tumor activity with a significant difference compared with that of the Compound X single-drug administration group and with that of the gefitinib single-drug administration group, was observed by a tumor volume inhibition rate of 73%. From these results, it became apparent that Compound X has anti-tumor activity against human non-small-cell lung cancer and that anti-tumor activity can be enhanced by its combined administration with an epidermal growth factor receptor (EGFR) inhibitor.

Test Example 6

Evaluation of In Vitro Cell Proliferation Inhibitory Activity Against Human Non-Small-Cell Lung Cancer Line by Combined Administration of a Compound Having PPARγ Activating Action with an Inhibitor of Vascular Endothelial Growth Factor Receptor (VEGFR) and Raf Kinase Effects of the combined administration of the compound described in Production Example 8 having PPARγ activating action (hereinafter referred to as Compound X), and a vascular endothelial growth factor receptor (VEGFR) and Raf kinase inhibitor, against human non-small-cell lung cancer line was studied by using cell proliferation inhibitory activity as an indicator.

Human non-small-cell lung cancer line A549 cells were inoculated on a 96-well plate at $5 \times 10^2$ cells/well, and at the same time, agents of various concentrations dissolved in DMSO were added so that the concentration of DMSO became 0.1%. Compound X was studied with a concentration of 10 μM, and for sorafenib (synthesized by Sankyo Company, Limited), which has VEGFR inhibitory activity and Raf kinase inhibitory activity, with a concentration of 5 μM (n=4). After addition of the drugs, the cells were cultivated in the presence of 5% carbon dioxide at 37° C. for 6 days. Then, Cell Titer 96 Aqueous One Solution Reagent (Promega Corp.) was added at 40 μl/well each, and then absorbance A490 of each well was measured using MICROPLATE READER (Bio-Rad Laboratories, Inc.). The average absorbance of each of the groups, which had been treated with respective concentrations of Compound X and sorafenib, was presented as a percentage expression, by taking the average absorbance of the compound non-addition control group (treated with DMSO only), as 100%. Accordingly, the cancer cell proliferation inhibitory activity of Compound X, sorafenib, and the combination of these were studied by subtracting this value from 100%.

The results are shown in Table 4.

TABLE 4

|  | Proliferation inhibition rate [%] |
| --- | --- |
| Compound X | 15 |
| Sorafenib | 47 |
| Compound X and sorafenib | 71** |

**P < 0.01, (combined administration group versus each of single-drug treated group, Students' t test)

As shown in Table 4, the single-drug treatment with Compound X (10 μM) showed a proliferation inhibition rate of 15%, and the single-drug treatment with sorafenib (5 μM) showed a proliferation inhibition rate of 47%; however, the combined administration of both drugs showed a proliferation inhibition rate of 71%. Here, the proliferation inhibition activity in the combined administration group showed a statistical difference, when compared with each of the single-drug treated groups. From these results, it became apparent that the combined administration of Compound X, and the vascular endothelial growth factor receptor (VEGFR) and Raf kinase inhibitor shows synergistic cancer cell proliferation inhibitory activity.

Test Example 7

Evaluation of in vivo anti-tumor activity against human kidney cancer by the combined administration of a compound having PPARγ activating action with an inhibitor of vascular endothelial growth factor receptor (VEGFR) and Raf kinase.

In vivo anti-tumor activity against human kidney cancer of the compound described in Production Example 8 having PPARγ activating action (hereinafter referred to as Compound X) was studied.

In the experiment, human kidney cancer line SN12-PM6 (provided by Professor Seiji Naito of Kyushu University), in which it was confirmed that no mouse pathogenic microorganism was detected by quarantine, was transplanted to a subcutaneous axillary portion of a nude mouse BALB/cA Jcl-nu (CLEA Japan, Inc.), to subculture a tumor. The tumor was cut into small pieces in a size of 5 mm, and transplanted to a right subcutaneous axillary portion of a BALE/cA Jcl-nu mouse by using a troker (CLEA Japan, Inc.). The required amounts of Compound X and sorafenib (synthesized by Sankyo Company, Limited), which has VEGFR inhibitory action and Raf kinase inhibitory action, were each weighed, and solutions were prepared by suspending Compound X in a 0.5%-methyl cellulose solution, and sorafenib in 50% ethanol (Kanto Chemical Co., Inc.)-50% cremophor (Sigma). Subsequently, distilled water (Otsuka Pharmaceutical Factory, Inc.) was added so that the final concentrations of ethanol and cremophor became each 12.5%. The solutions were prepared so that the final concentrations of Compound X and sorafenib became 0.3 mg/mL and 10 mg/mL respectively. Each of these compound administration solutions was administered orally to a SN12-PM6 tumor-bearing nude mouse using a sonde (Fuchigami Kikaiten) from 10 days after the transplantation of the tumor, once a day, 5 times per week, until 56 days after transplantation, in the amount of 0.1 mL per 10 g of mouse weight. Twice a week, the major axis and the minor axis of the transplanted tumor were measured using digital micrometer calipers (MAX-CAL MAX-15: Nihon Sokutei Kougu Kabusikikaisha), and tumor proliferation inhibitory activity was obtained from the following calculation formula and expressed as the tumor volume inhibition rate.

Average tumor volume in each test group (mm$^3$)=½×(minor axis)$^2$ (mm$^2$)×(major axis)(mm)

Tumor volume inhibition rate (%)={1−(average tumor volume of drug administration group/average tumor volume of drug non-administration group)}×100

Evaluation of anti-tumor activity for each of the drug administration group was determined by the tumor volume inhibition rate. In addition, a statistical difference test was determined by conducting Students' t test with respect to the tumor volumes of the drug non-administration control group and the drug administration group 59 days after transplantation. Here, it was determined that there is a significant difference between the two groups when p value is less than 0.05.

The results are shown in FIG. 5.

As shown in FIG. 5, Compound X significantly inhibited proliferation of human kidney cancer line SN12-PM6 by single-drug administration (tumor volume inhibition rate of 37%). In addition, single-drug administration of sorafenib also showed significant proliferation inhibitory activity (tumor volume inhibition rate of 43%). On the other hand, when Compound X and sorafenib were administered in combination, enhancement in anti-tumor activity with a significant difference compared with that of the Compound X single-drug administration group and with that of the sorafenib single-drug administration group was observed by a tumor volume inhibition rate of 65%. From these results, it became apparent that Compound X has anti-tumor activity against human kidney cancer and that anti-tumor activity can be enhanced by its combined administration with a vascular endothelial growth factor receptor (VEGFR) and Raf kinase inhibitor.

Figure 1:
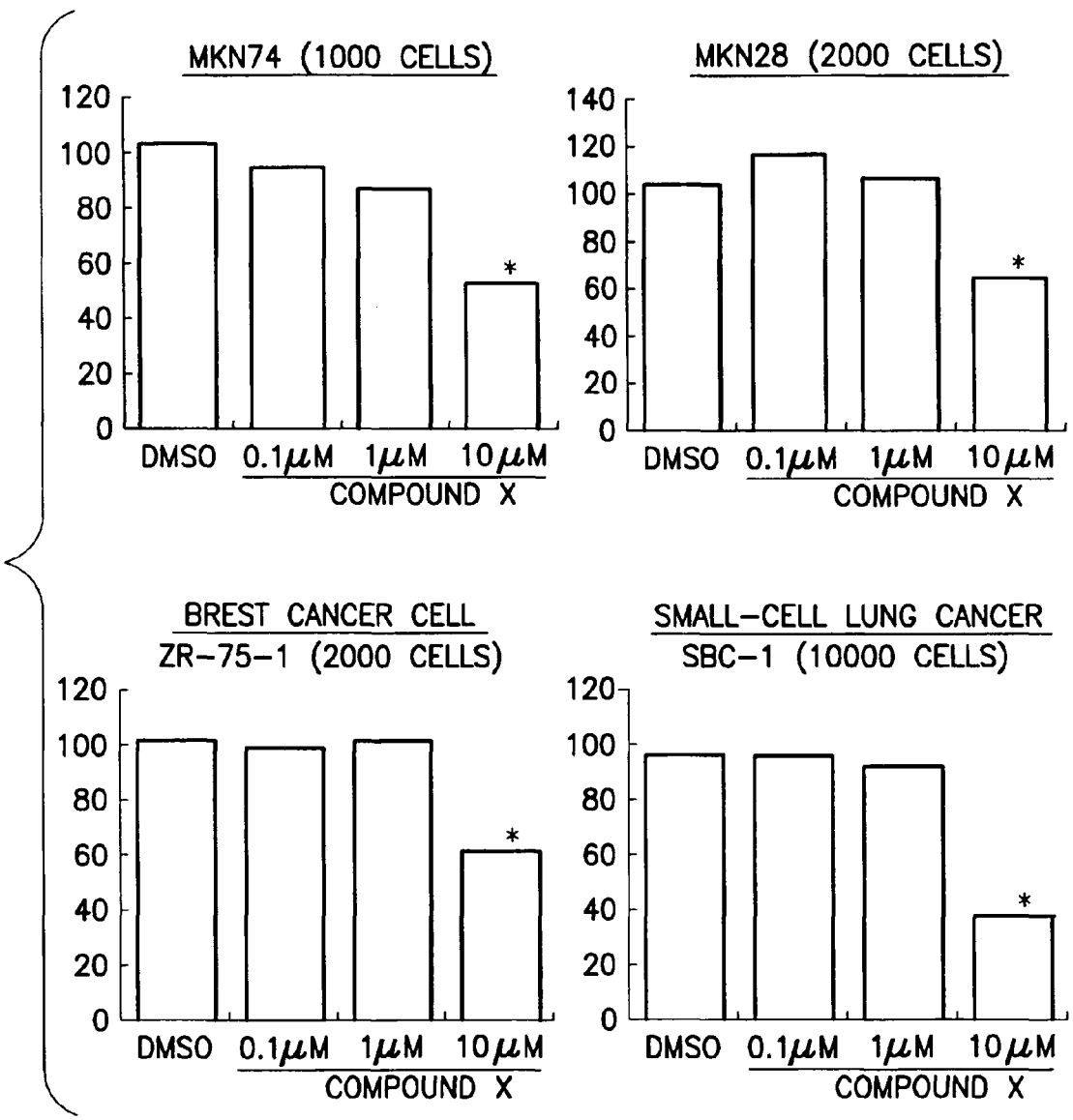
[FIG. 1] This is a graph showing the relationship between the concentration of Compound X and cancer cell proliferation inhibitory activity, in which plotting is made by taking the absorbance (%) of each of the cells after addition of Compound X to each of the cancer cells as the longitudinal axis, and the concentration (μM) of Compound X added as the horizontal axis.
Figure 2:
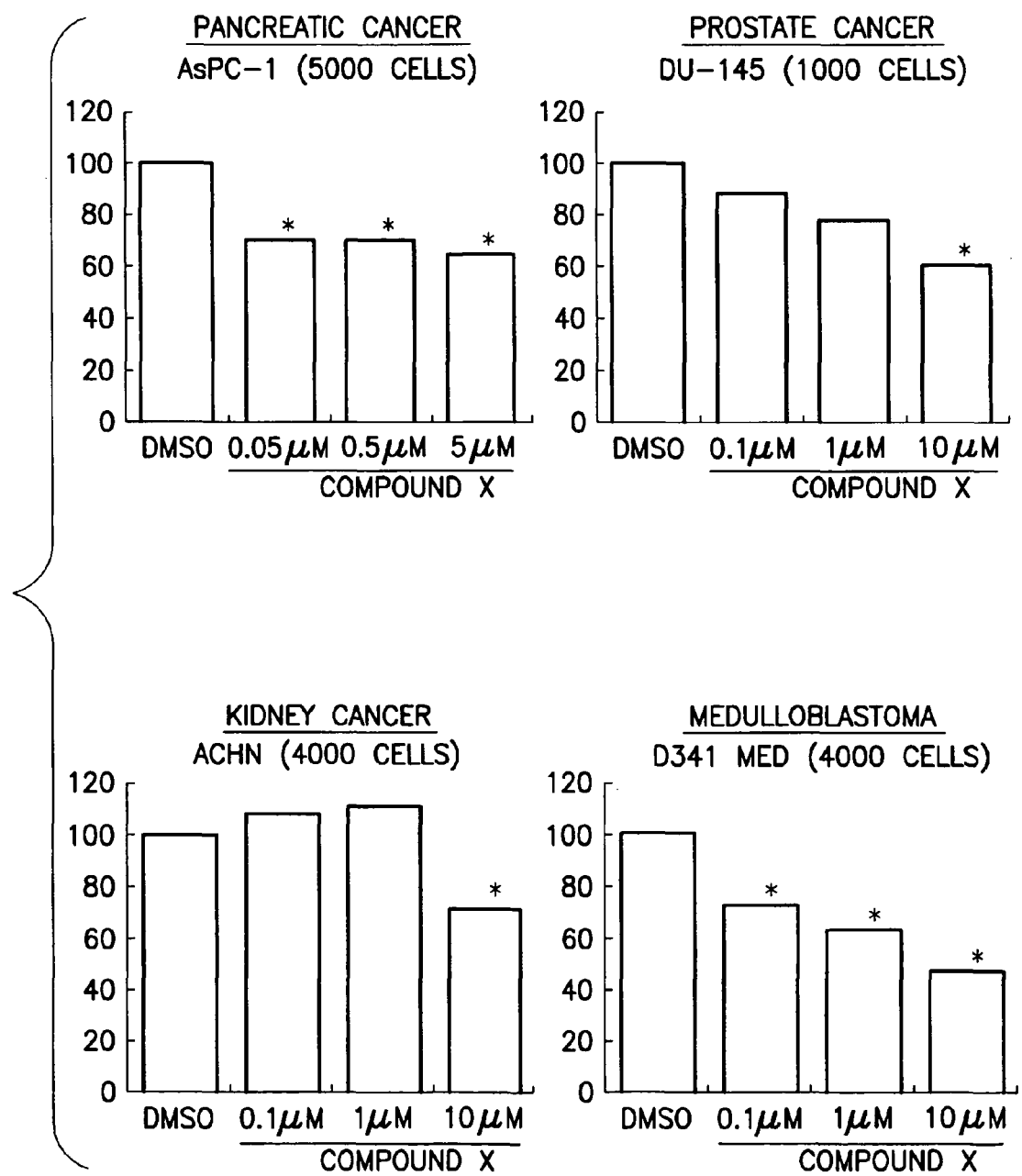
[FIG. 2] This is a graph showing the relationship between the concentration of Compound X and cancer cell proliferation inhibitory activity, in which plotting is made by taking the absorbance (%) of each of the cells after addition of Compound X to each of the cancer cells as the longitudinal axis, and the concentration (μM) of Compound X added as the horizontal axis.
Figure 3:
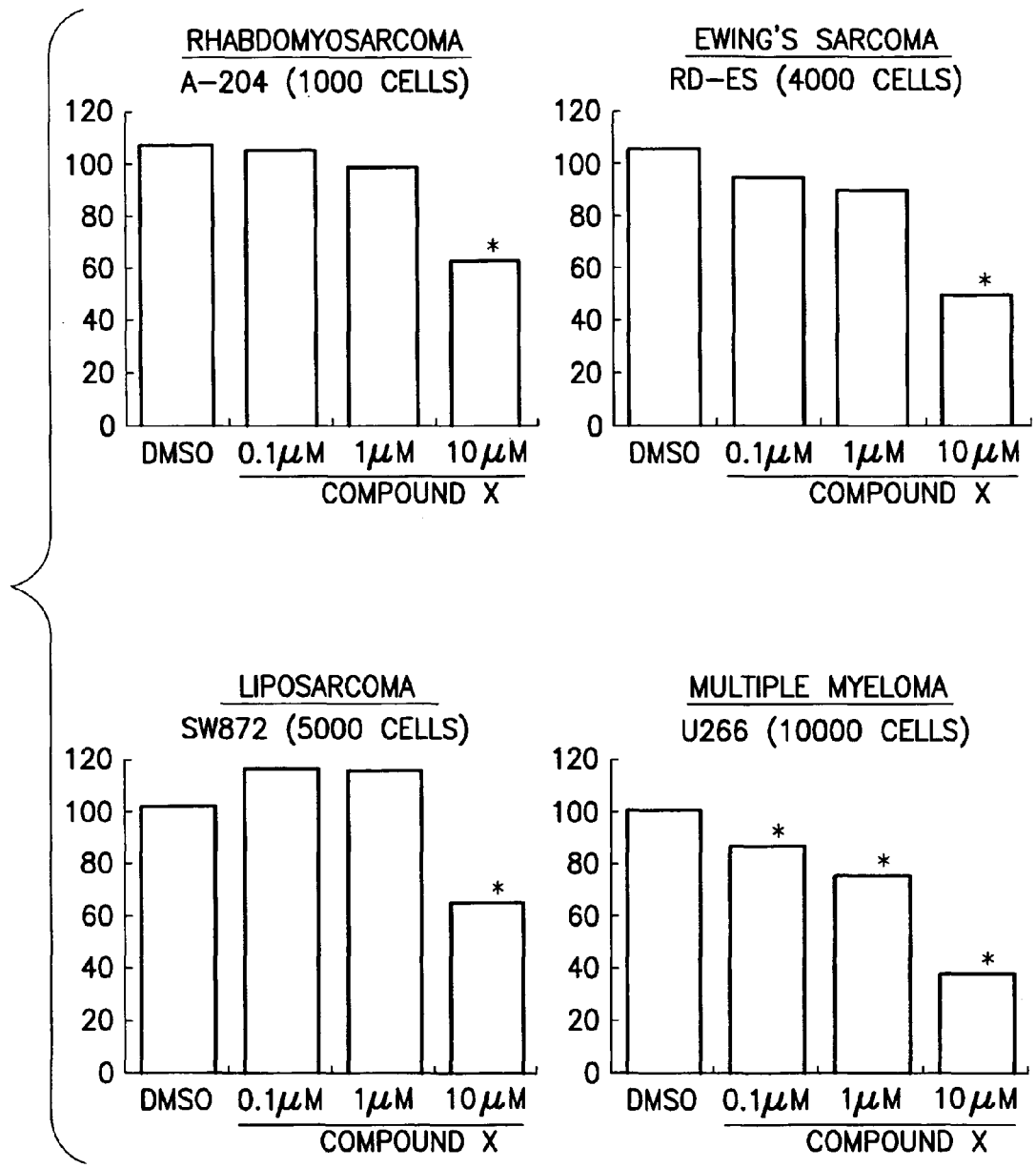
[FIG. 3] This is a graph showing the relationship between the concentration of Compound X and cancer cell proliferation inhibitory activity, in which plotting is made by taking the absorbance (%) of each of the cells after addition of Compound X to each of the cancer cells as the longitudinal axis, and the concentration (μM) of Compound X added as the horizontal axis.
Figure 4:
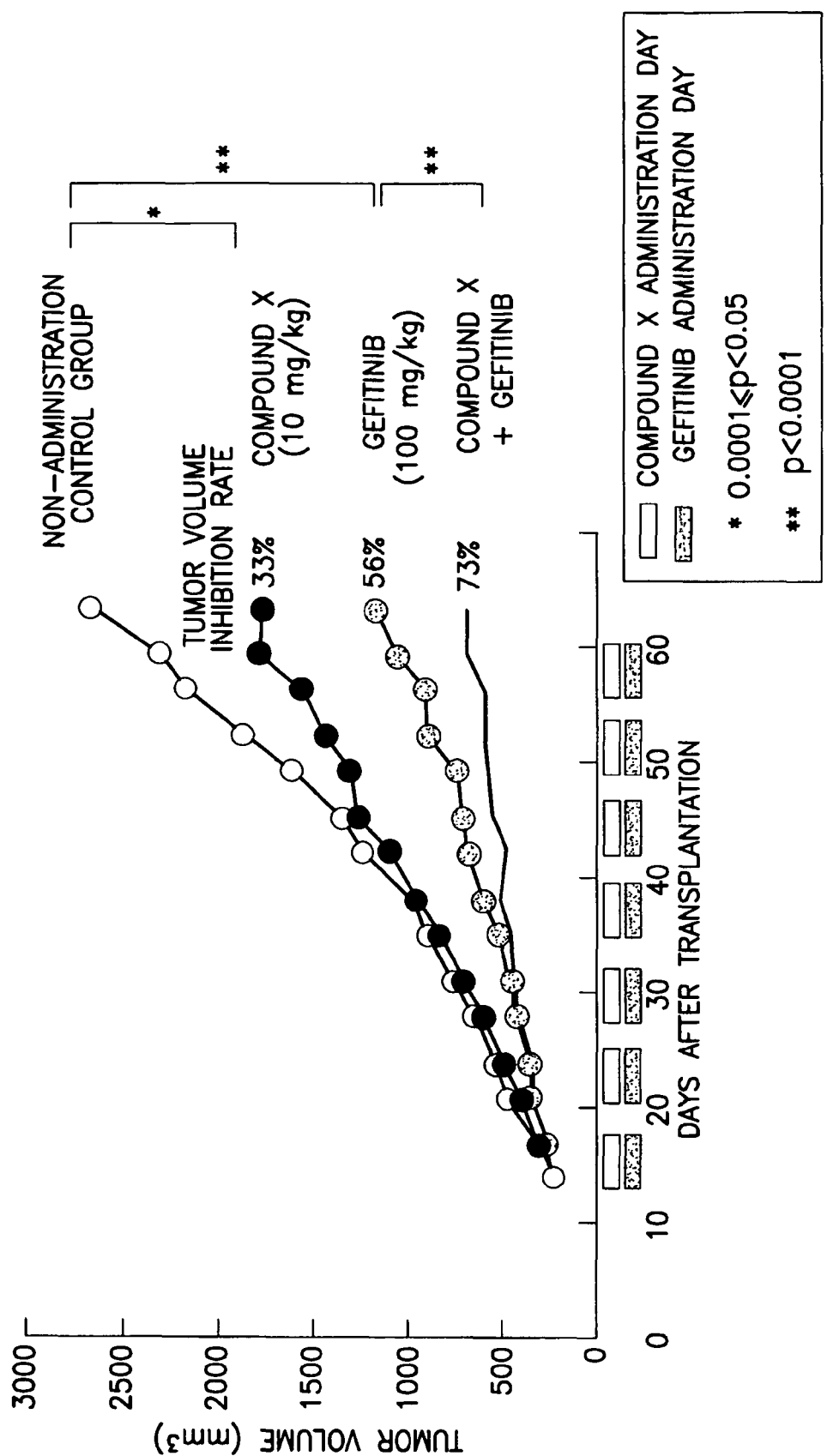
[FIG. 4] This is a graph showing the relationship between days after transplantation and tumor volume, in which plotting is made by taking the tumor volume (mm$^3$), for the cases where Compound X alone, gefitinib alone, or the combination of both drugs was used for the transplanted cancer cells, as the longitudinal axis, and the days after transplantation (day) as the horizontal axis.
Figure 5:
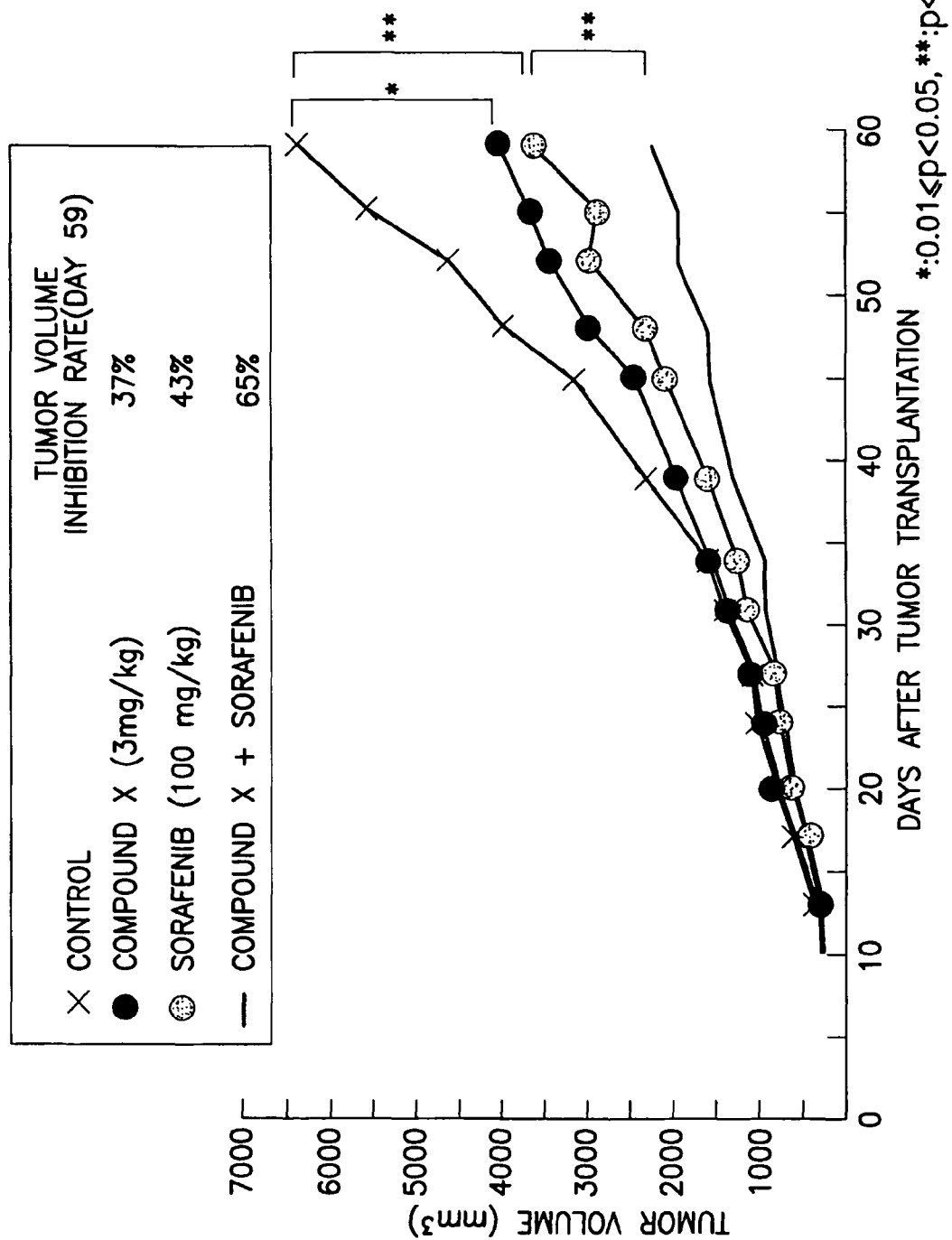
[FIG. 5] This is a graph showing the relationship between days after transplantation and tumor volume, in which plotting is made by taking the tumor volume (mm$^3$), for the cases where Compound X alone, sorafenib alone, or the combination of both drugs was used for transplanted cancer cells, as the longitudinal axis, and the days after transplantation (day) as the horizontal axis.

We claim:

1. An anti-cancer pharmaceutical composition for the treatment of lung cancer, comprising (a) an effective amount of erlotinib; and (b) an effective amount of 5-(4-(6-(4-amino-3,5-dimethyl-phenoxy)-1-methyl-1H-benzimidazol-2-yl-methoxy)-benzyl)-thiazolidine-2,4-dione.dihydrochloride; as active ingredients.

2. A method of treating a person having lung cancer comprising administering to said person (a) an effective amount of erlotinib and (b) an effective amount of 5-(4-(6-(4-amino-3,5-dimethyl-phenoxy)-1-methyl-1H-benzimidazol-2-yl-methoxy)-benzyl)-thiazolidine-2,4-dione.dihydrochloride.

* * * * *